(12) United States Patent
Oakley et al.

(10) Patent No.: US 8,556,030 B2
(45) Date of Patent: Oct. 15, 2013

(54) ULTRASONIC ATTENUATION MATERIALS

(75) Inventors: Clyde Gerald Oakley, Centennial, CO (US); Michael J. Shepard, Flagstaff, AZ (US); Michael J. Zipparo, Parker, CO (US); Hermann Scholz, Ottobrunn (DE)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/093,059

(22) Filed: Apr. 25, 2011

(65) Prior Publication Data

US 2011/0198151 A1 Aug. 18, 2011

Related U.S. Application Data

(62) Division of application No. 11/694,453, filed on Mar. 30, 2007, now Pat. No. 7,956,514.

(51) Int. Cl.
*E04B 1/84* (2006.01)

(52) U.S. Cl.
USPC ............................................ 181/294; 181/284

(58) Field of Classification Search
USPC .................................................. 181/294, 284
See application file for complete search history.

(56) References Cited

U.S. PATENT DOCUMENTS

| | | | | |
|---|---|---|---|---|
| 2,097,054 A * | 10/1937 | Clarke | | 106/674 |
| 4,187,390 A | 2/1980 | Gore | | |
| 4,381,470 A | 4/1983 | Leach et al. | | |
| 4,571,520 A | 2/1986 | Saito et al. | | |
| 4,607,466 A * | 8/1986 | Allred | | 52/144 |
| 4,695,501 A | 9/1987 | Robinson | | |
| 4,798,756 A | 1/1989 | Fukushima et al. | | |
| 5,212,355 A * | 5/1993 | Edwards et al. | | 181/290 |
| 5,329,498 A | 7/1994 | Greenstein | | |
| 5,476,598 A | 12/1995 | Schramm, Jr. et al. | | |
| 5,632,844 A * | 5/1997 | Pate et al. | | 156/290 |
| 5,648,941 A | 7/1997 | King | | |
| 5,744,763 A * | 4/1998 | Iwasa et al. | | 181/286 |
| 6,156,682 A * | 12/2000 | Fletemier et al. | | 442/394 |
| 6,345,688 B1 * | 2/2002 | Veen et al. | | 181/290 |
| RE39,260 E * | 9/2006 | Byrd et al. | | 181/290 |
| 7,956,514 B2 * | 6/2011 | Oakley et al. | | 310/322 |
| 2003/0066708 A1 * | 4/2003 | Allison et al. | | 181/290 |
| 2005/0225210 A1 | 10/2005 | Englund et al. | | |
| 2005/0263345 A1 * | 12/2005 | Erickson et al. | | 181/290 |
| 2006/0261707 A1 | 11/2006 | Wildes et al. | | |
| 2006/0273695 A1 | 12/2006 | Savage | | |
| 2009/0009035 A1 * | 1/2009 | Yamashita et al. | | 310/327 |
| 2010/0133039 A1 * | 6/2010 | Liguore | | 181/294 |
| 2010/0300801 A1 * | 12/2010 | Maeder | | 181/294 |
| 2011/0186381 A1 * | 8/2011 | Ogawa et al. | | 181/294 |

* cited by examiner

*Primary Examiner* — Forrest M Phillips
(74) *Attorney, Agent, or Firm* — Amy L. Miller

(57) ABSTRACT

Improved acoustic attenuation materials and applications are provided. An improved acoustic attenuation material may include a woven layer of fibers made of porous polymers, such as porous polytetrafluoroethylene (PTFE), that include interstitial space. An improved acoustic attenuation material may include sheets of porous polymers interleaved with layers of epoxy. The sheets of porous polymers may include through holes. An embodiment of an ultrasonic transducer that includes a backing with woven layers of porous PTFE fibers is provided. The ultrasonic transducer that includes a backing with woven layers of porous PTFE fibers may be used in a three-dimensional ultrasound imaging apparatus. An embodiment of an ultrasonic transducer that includes a plurality of sheets of porous PTFE interleaved with layers of epoxy is provided. The ultrasonic transducer that includes a plurality of sheets of porous PTFE may be used in an ultrasonic imaging catheter.

21 Claims, 19 Drawing Sheets

ULTRASONIC ATTENUATION MATERIALS

RELATED APPLICATION

The present application is a divisional application of allowed U.S. patent application Ser. No. 11/694,453 filed Mar. 30, 2007 now U.S. Pat. No. 7,956,514.

BACKGROUND

Acoustic attenuation materials are used in a wide variety of applications where it is desired to attenuate acoustic signals. Acoustic attenuation material may be used, for example, in soundproofing materials used in architectural applications. Many such acoustic attenuation materials require considerable volume to achieve desired levels of attenuation.

Acoustic attenuation materials are also incorporated into relatively small devices where control of acoustic energy is required. One such application is in the field of ultrasound imaging probes. Ultrasound imaging probes continue to enjoy widespread use in the medical field. By way of example, ultrasound probes are utilized for a wide variety of external, laparoscopic, endoscopic and intravascular imaging applications. The ultrasound images provided by imaging probes may, for example, be used for diagnostic purposes.

Ultrasound imaging probes typically include a plurality of parallel piezoelectric transducer elements arranged along a longitudinal axis, with each element interconnected to a pair of electrodes. Typically, the transducers are subdivided in the longitudinal direction by dicing during production, resulting in independent transducer elements that enable electronic steering and focusing within an imaging plane. An electronic circuit, interconnected to the electrodes, excites the transducer elements causing them to emit ultrasonic energy. The transducer elements may be operable to convert received ultrasonic energy into electrical signals, which may then be processed and used to generate images.

Typically, the transducers include an active layer of a piezoelectric material with an acoustic face from which acoustic signals are emitted. Often an acoustic damping member is disposed rearward of the active layer on an opposite side of the active layer from the acoustic face. The acoustic damping member serves to damp undesirable acoustic signals (e.g., signals that may emanate from and be reflected back to the rear face of the transducer) that may interfere with the acoustic signals received at the acoustic face. As may be appreciated, for a particular acoustic damping material, acoustic damping capabilities typically increase as the volume of the acoustic damping member increases. Accordingly, as the acoustic damping member is reduced in volume, the acoustic damping capabilities typically decrease. Consequently, the overall volume and mass of an ultrasound probe that includes an ultrasonic transducer and acoustic damping member may be at least partially dependent on the acoustic damping capabilities of the material of the acoustic damping member.

SUMMARY

As the applications for, and use of, ultrasound imaging probes continue to expand, so does the need for ultrasound probe designs that yield higher imaging performance, greater miniaturization, and/or increased production efficiencies. In this regard, the ability to realize enhanced performance, miniaturization and production efficiencies related to ultrasound imaging probes through improvements to acoustic attenuation materials used in ultrasound imaging probes becomes particularly significant. Moreover, there exists a need for improved acoustic attenuation materials in general.

In view of the foregoing, an object of embodiments described herein may be to provide improved acoustic attenuation materials. An additional objective may be to provide improved ultrasonic transducer systems utilizing improved acoustic attenuation materials.

In one aspect, an acoustic attenuation material is provided operable to attenuate acoustic energy incident upon the material. The material may include a first component comprised of a first polymer having a porosity and a second component comprised of a second polymer. The porosity of the first component may be partially filled with the second component. The first component may have a first flexural modulus when its porosity is free from the second component and a second flexural modulus when the second component is partially disposed within its porosity. The first flexural modulus may be lower than the second flexural modulus. The first component may be comprised of a woven and/or non-woven porous polymer.

In another aspect, an acoustic attenuation material comprising a first layer adapted for use in attenuating acoustic energy having a frequency between 100 kHz and 100 MHz is provided. The first layer may have a first stiffness and a first acoustic attenuation. The acoustic attenuation material may also include a second layer having a second stiffness and a second acoustic attenuation. The first stiffness may be less than the second stiffness and the first acoustic attenuation may be at least two times greater than the second acoustic attenuation. The first layer may be comprised of woven and/or non-woven porous polymer.

In a related aspect, an acoustic attenuation material including a woven layer is operable to attenuate acoustic energy incident upon the material. The woven layer may be comprised of a plurality of fibers. The fibers may be comprised of porous polytetrafluoroethylene (PTFE). The woven layer may define void space between the fibers that may be at least partially filled with fluorothermoplastic (THV).

In still another aspect, an acoustic attenuation material is provided that is operable to attenuate acoustic energy incident upon the material that is comprised of a plurality of non-woven membranes and a plurality of support layers. The non-woven membranes may be comprised of a porous polymer. The plurality of non-woven membranes may be interleaved with the plurality of support layers. The support layers may be comprised of a support material. The support material may be porous or non-porous. The support layers may be porous or non-porous.

In a further aspect, an acoustic attenuation material is provided that is configured such that a sound beam traveling from a first side of the material to a second side of the material must pass through at least a portion of a porous polymer. A reinforcing material may also be included in the acoustic attenuation material. The acoustic attenuation of the porous polymer may be at least twice that of the reinforcing material.

In another aspect, a method is provided that includes the steps of placing a member comprising a layer of porous polymer in the path of acoustic energy to be attenuated, absorbing at least a portion of the acoustic energy within the member and supporting the layer of porous polymer with at least one layer of a support material. The porous polymer may be woven and/or non-woven. The method may further include locating a front side of the material adjacent to a surface and absorbing both energy emanating from the surface and energy incident upon a back side of the material within the material.

The method may also include attenuating acoustic energy within a predetermined volume by placing the material within the predetermined volume.

In still another aspect, an acoustic attenuation material is provided comprising a woven layer adapted for use in an ultrasonic transducer apparatus and a reinforcing material. The woven layer may be operable to attenuate acoustic energy incident upon it. The woven layer may be comprised of a plurality of porous fibers that define void space between the plurality of fibers. The reinforcing material may at least partially fill the void space.

An embodiment may include a second woven layer comprising a second plurality of fibers. The second plurality of fibers may be porous and may define second woven layer void space. The reinforcing material may at least partially fill the second woven layer void space. In various embodiments, a layer of epoxy may be disposed between two woven layers.

In an embodiment, the reinforcing material may comprise epoxy, THV, Fluorinated Ethylene-Propylene (FEP), PTFE, polyethersufone (PES), ethylene-FEP copolymer (EFEP), polyester thermoplastic (PET), polyetheretherketone (PEEK), polyetherimide (PEI), polycarbonate (PC), liquid crystal polymer (LCP) or any combination thereof. In an embodiment, the plurality of fibers may comprise a porous polymer selected from a group consisting of PTFE, urethane, polystyrene, fluoropolymer, silicone and polyolefin.

The acoustic attenuation material may, in an embodiment, be operable to attenuate acoustic energy in the ultrasonic range. For example, the acoustic attenuation material may be operable to attenuate acoustic energy between 100 kHz and 100 MHz.

In another aspect, an ultrasound transducer system is provided comprising an active layer and an acoustic attenuation layer. The active layer may have an acoustic face and a rear face (opposite of the acoustic face) and include at least one ultrasonic transducer element. The acoustic attenuation layer may comprise a porous polymer and a reinforcing material and be interconnected to the rear face of the active layer. In an arrangement, the reinforcing material may be partially imbibed into the porosity of the porous polymer.

In an embodiment, the ultrasonic transducer elements may be operable to transmit ultrasonic signals, receive ultrasonic signals, or both transmit and receive ultrasonic signals. At least one of the ultrasonic transducer elements may be planar. At least one of the ultrasonic transducer elements may be curved. In an embodiment, the reinforcing material may include a thermoplastic material and/or a thermoset material.

The ultrasound transducer system of various embodiments may include an intermediate layer disposed between the rear face of the active layer and the acoustic attenuation layer. The intermediate layer may comprise epoxy, silicone rubber, tungsten, aluminum oxide, mica, microspheres, or any combination thereof.

In yet another aspect, an ultrasound transducer system is provided comprising an active layer and an acoustic attenuation layer. The active layer may have an acoustic face and a rear face (opposite of the acoustic face) and include at least one ultrasonic transducer element. The acoustic attenuation layer may include a woven layer of porous polymer fibers and a reinforcing material and be interconnected to the rear face of the active layer. The reinforcing material may at least partially fill void space between fibers of the acoustic attenuation layer. In an arrangement, the acoustic attenuation layer may contain multiple woven layers with layers of adhesive between adjacent acoustic attenuation layers to bind the acoustic attenuation layers together.

An embodiment may include an electrical connection member. The electrical connection member may be comprised of an insulating material and a plurality of independent electrically conductive pathways. Each of the plurality of electrically conductive pathways may be disposed transverse to and in electrical contact with a corresponding one of the at least one ultrasonic transducer elements.

In an arrangement, the backing may include a plurality of continuous pathways through the backing. The passageways may be at least partially filled with an electrically conductive material and provide an electrically conductive path through the backing.

In another aspect, an ultrasound transducer system is provided comprising an active layer and a backing. The active layer may have an acoustic face and a rear face (opposite of the acoustic face) and include at least one ultrasonic transducer element. The backing may include a support material. The backing may include at least one non-woven membrane comprised of a porous polymer interleaved with a plurality of support layers comprised of the support material.

In an embodiment, the non-woven membranes may contain a plurality of through holes at least partially filled with the support material. Adjacent non-woven membranes may be arranged such that at least some of the plurality of through holes of a particular non-woven membrane are free from alignment with any of the through holes of an adjacent non-woven membrane. Adjacent non-woven membranes may be arranged such that most or all of the plurality of through holes of a particular non-woven membrane are free from alignment with any through holes of an adjacent non-woven membrane. In an embodiment, each of the non-woven membranes may be less than 200 microns (e.g., between 1 and 200 microns) thick and each of the plurality of support layers may be less than 200 microns (e.g., between 1 and 200 microns) thick.

In an embodiment, each of the membranes and support layers may be oriented parallel to the active layer. In another embodiment, each of the membranes and support layers may be oriented at an angle relative to the active layer.

In an embodiment, the membranes and support layers may be free from through holes. In such an arrangement, each of the non-woven membranes may be less than 800 microns (e.g., between 1 and 800 microns) thick and each of the plurality of support layers may be less than 500 microns (e.g., between 1 and 500 microns) thick. Also, in such an arrangement, the support material may be comprised of polymer, ceramic, metal or any combination thereof. The support material may be porous or non-porous. The plurality of support layers may be porous or non-porous. In embodiments where the support material comprises polymer, the polymer may be thermoset, thermoplastic, fluoropolymer, epoxy or any combination thereof. Furthermore, a plurality of interconnection layers may be disposed between adjacent membranes and support layers. The interconnection layers may comprise a carrier with adhesive disposed on both sides. The interconnection layers may bind adjacent membranes and support layers together.

In still another aspect, an ultrasound transducer system is provided comprising an active layer and a backing. The active layer may have an acoustic face and a rear face (opposite of the acoustic face) and include at least one ultrasonic transducer element. The backing may include a first side and a second side oppositely disposed from the first side. The backing may be interconnected to the rear face of the active layer. The backing may include porous polymer and reinforcing material and be configured such that a sound beam traveling from the first side to the rear face of the ultrasonic transducer element must pass through at least a portion of the porous polymer. The porous polymer and reinforcing material may be selected such that the overall flexural modulus of the backing is at least twice that of the porous polymer alone. With respect to sound beams traveling from the first side to the rear face, the backing may have an acoustic attenuation of at least 25 dB/cm at 1 MHz. The porous polymer and reinforcing material may be selected such that the acoustic attenuation of the porous polymer is at least twice that of the reinforcing material.

In another aspect, an ultrasound transducer system is provided comprising an active layer and a backing. The active layer may have an acoustic face and a rear face (opposite of the acoustic face) and include at least one ultrasonic transducer element. The backing may include a plurality of membranes comprised of a porous polymer interleaved with a plurality of support layers comprised of a support material. The plurality of membranes may include a plurality of sections from which portions of the plurality of membranes have been removed.

Adjacent membranes may be arranged such that some, most, or all of the plurality of sections from which portions of the plurality of membranes have been removed of a particular membrane are free from alignment with any of the through holes of an adjacent membrane.

In even another aspect, a method of reducing acoustic energy incident on a back face of an ultrasound transducer is provided. The method may include providing a layer of material comprising a porous polymer, locating the layer of material adjacent to a back face of an ultrasound transducer and absorbing acoustic energy within the layer of material. The layer of material may have a front surface and a rear surface. The front surface may be in face to face contact with the back face of the ultrasound transducer while the rear surface may be in contact with a fluid. The absorbing may include absorbing acoustic energy emanating from the back face of the ultrasound transducer and absorbing acoustic energy incident upon the rear surface of the layer of material.

In an embodiment, the fluid may be a gas or a liquid. In an embodiment, the layer of material may comprise at least one woven layer of porous polymer fibers wherein void space between the porous polymer fibers is at least partially filled with a non-porous polymer.

In another aspect, a method of reducing acoustic energy incident on a back face of an ultrasound transducer is provided. The method may include providing an acoustic attenuation member that includes a non-woven porous polymer layer and a support material, locating the acoustic attenuation member adjacent to a back face of an ultrasound transducer and absorbing acoustic energy within the acoustic attenuation member. The acoustic attenuation member may have a front surface and a rear surface. The front surface may be in face to face contact with the back face of the ultrasound transducer. The absorbing may include absorbing, within the acoustic attenuation member, acoustic energy emanating from the back face of the ultrasound transducer and acoustic energy incident upon the rear surface of the acoustic attenuation member.

In an embodiment, the acoustic attenuation member may comprise a plurality of non-woven porous polymer layers interleaved with a plurality of layers of the support material. The plurality of non-woven porous polymer layers may include a plurality of holes.

In yet another aspect, an ultrasonic catheter probe is provided that includes an ultrasound transducer disposed within an outer shell. The ultrasound transducer includes an active layer with an acoustic face and a rear face opposite from the acoustic face. The active layer may comprise at least one ultrasonic transducer element. The ultrasound transducer may further include a backing interconnected to the rear face. The backing may comprise a plurality of acoustic attenuation layers interleaved with a plurality of support layers.

In an embodiment, the plurality of acoustic attenuation layers may comprise a porous polymer. In an embodiment, the plurality of acoustic attenuation layers may include a plurality of vias therethrough. The plurality of vias may be at least partially filled with a support material.

In still another aspect, an acoustic attenuation device comprising an acoustic attenuation material and a support structure interconnected to the acoustic attenuation material is provided. The acoustic attenuation material may be operable to attenuate acoustic energy incident upon the material and may include a first component comprised of a porous polymer and a second component comprised of a support material. The first component may be woven and/or non-woven.

In an arrangement, the porosity of the porous polymer may be partially filled with the second component. In an arrangement, the first component may be comprised of a woven layer of porous fibers.

In an embodiment, the first component may include a plurality of non-woven membranes and the second component may comprise a plurality of support layers. The membranes and support layers may be interleaved. In an embodiment, each of the plurality of membranes may include a plurality of vias defining a plurality of passageways through the plurality of membranes. The plurality of vias may be at least partially filled with the support material.

The various features discussed above in relation to each aforementioned aspect may be utilized by any of the aforementioned aspects. Additional aspects and corresponding advantages will be apparent to those skilled in the art upon consideration of the further description that follows.

DETAILED DESCRIPTION

Figure 1:
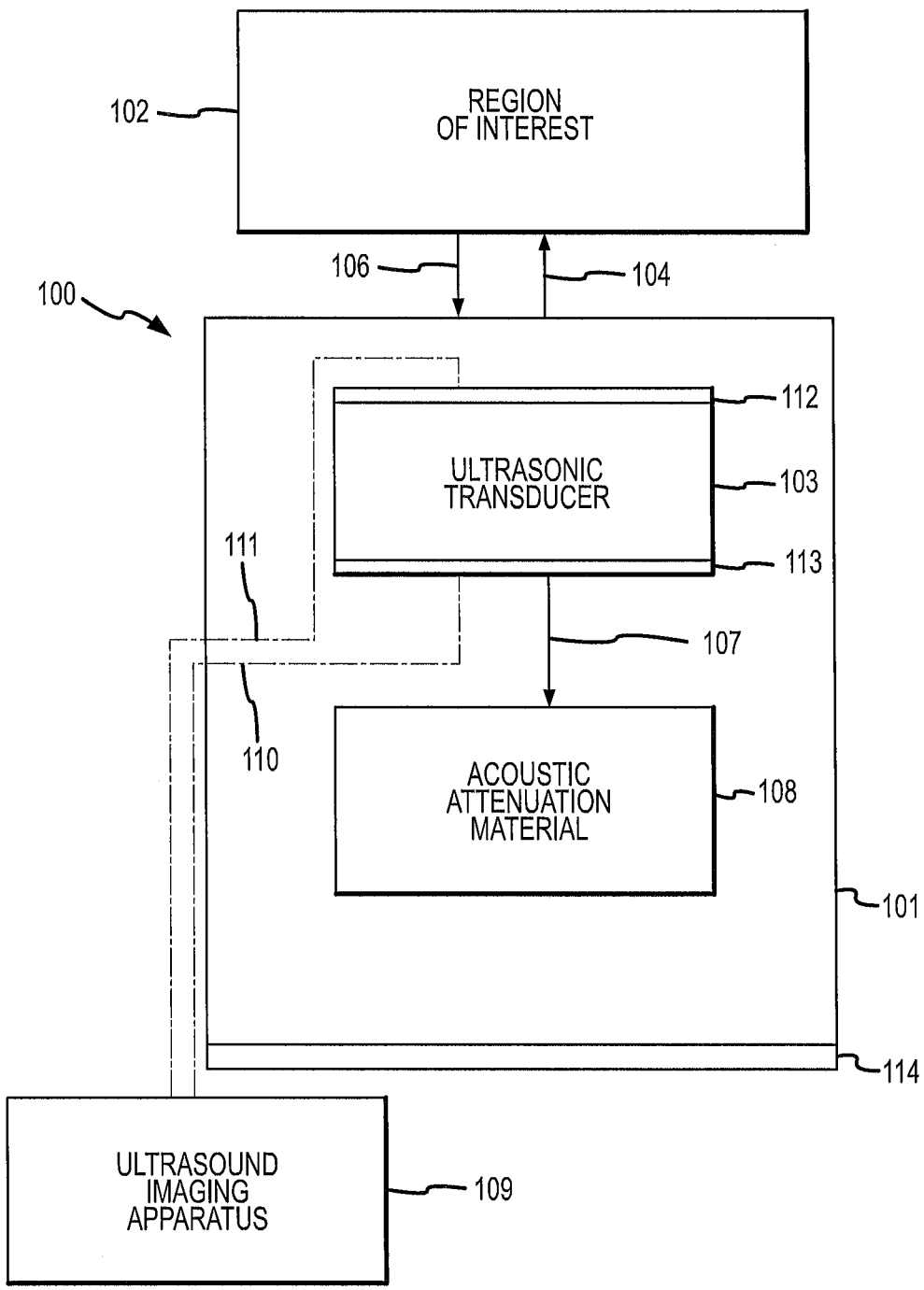
FIG. 1 is a schematic diagram of an embodiment of an ultrasound probe and a region of interest.

FIG. 1 is a schematic diagram of an embodiment of an ultrasound probe 100, an ultrasound imaging apparatus 109 and a region of interest 102. The ultrasound probe 100 includes at least one ultrasonic transducer 103. The ultrasonic transducer 103 may be a mechanically active layer operable to convert electrical energy to mechanical (e.g., acoustic) energy and/or convert mechanical energy into electrical energy. For example, the ultrasonic transducer 103 may be operable to convert electrical signals from the ultrasound imaging apparatus 109 into ultrasonic acoustic energy. Furthermore, the ultrasonic transducer 103 may be operable to convert received ultrasonic acoustic energy into electrical signals. The ultrasonic transducer 103 may comprise at least one ground electrode 112 and at least one signal electrode 113. The at least one signal electrode 113 and the at least one ground electrode 112 may be electrically interconnected to the ultrasound imaging apparatus 109 by at least one signal connection 110 (e.g., at least one signal wire) and at least one ground connection 111 (e.g., at least one ground wire), respectively. The ultrasonic transducer 103 may comprise an array of individual transducer elements that may each be electrically connected to the ultrasound imaging apparatus 109 via a signal connection and a ground connection. The array may be a one-dimensional array that includes a single row of individual transducer elements. The array may be a two-dimensional array that includes individual transducer elements arranged, for example, in multiple columns and multiple rows Ground connections of the entire array may be aggregated and be electrically connected to the ultrasound imaging apparatus 109 through a single ground connection.

To generate an ultrasound image, the ultrasound imaging apparatus 109 may send electrical signals to the ultrasonic transducer 103 which in turn may convert the electrical energy to ultrasonic acoustic energy 104 which may be emitted toward a region of interest 102. The region of interest 102 may be an internal structure of a patient, such as an organ. The structure within the region of interest 102 may reflect a portion of the acoustic energy 106 back toward the ultrasonic transducer 103. The reflected acoustic energy 106 may be converted to electrical signals by the ultrasonic transducer 103 which may be sent to the ultrasound imaging apparatus 109 where the signals may be processed and an image of the region of interest 102 may be generated.

The process of converting the electrical signals from the ultrasound imaging apparatus 109 into ultrasonic acoustic energy 104 directed toward the region of interest 102 may also produce additional acoustic energy 107 directed in directions other than toward the region of interest 102. This additional acoustic energy 107 may reflect off of various structures, such as the housing 101 of the ultrasound probe 100, and return to the ultrasonic transducer 103 where it may be converted to electrical signals. The electrical signals from the reflected additional acoustic energy 107 may interfere with the electrical signals from the reflected acoustic energy 106. Such interference may result in image quality degradation.

To reduce interference from the reflected additional acoustic energy 107, acoustic attenuation material 108 may be included in the ultrasound probe 100. The acoustic attenuation material 108 may be interconnected to the ultrasonic transducer 103 along a surface of the ultrasonic transducer 103 opposite from the surface of the ultrasonic transducer 103 facing the region of interest 102 (e.g., a back surface of the ultrasonic transducer 103). The acoustic attenuation material 108 may prevent a substantial amount of the additional acoustic energy 107 from returning to the back surface of the ultrasonic transducer 103. The acoustic attenuation material 108 may also reduce the amount of acoustic energy reaching the back surface of the ultrasonic transducer 103 from other sources. In this regard, the acoustic attenuation material 108 may provide for reduced interference and enhanced image quality. In embodiments where the acoustic attenuation material 108 is connected directly to the ultrasonic transducer 103, the at least one signal connection 110 may pass through the acoustic attenuation material 108.

Furthermore, acoustic attenuation material may be positioned in other locations within the ultrasound probe 100 to attenuate acoustic energy within the ultrasound probe 100. For example, an amount of acoustic attenuation material 114 may be placed against the housing 101 to dampen (e.g., absorb) acoustic energy that may otherwise reflect off of an inner surface of the housing 101 and reduce image quality. Although illustrated as lining one entire side of the inside of the housing 101 in FIG. 1, the acoustic attenuation material 114 may be placed along any internal surface or portion thereof of the housing 101 where it may be beneficial to attenuate acoustic energy. The acoustic attenuation material 114 may also be located adjacent to other structures within the ultrasound probe 100 (e.g., circuit boards) to attenuate acoustic energy that could otherwise reflect off of those other structures.

Figure 2:
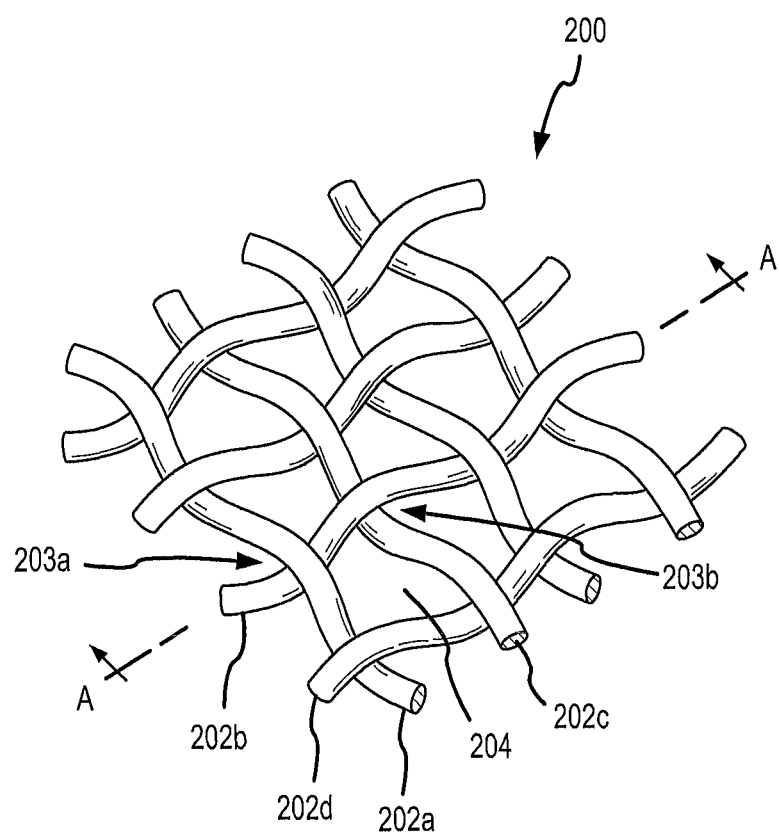
FIG. 2 illustrates an embodiment of a woven layer of fibers.

Embodiments of acoustic attenuation materials that may be used for attenuating acoustic energy, including attenuating ultrasonic energy in ultrasound probes will now be described. FIG. 2 is an illustration of a woven layer 200 that may be used in an acoustic attenuation material. The woven layer 200 may be comprised of a plurality of individual fibers, such as individual fibers 202a, 202b, 202c and 202d. FIG. 2 illustrates an example of a type of weave where individual fibers, such as individual fibers 202a, 202b, 202c and 202d, alternate position relative to each other. For example, fiber 202b alternates between being below fiber 202a (as oriented in FIG. 1) at a first intersection 203a and above fiber 202c at a second intersection 203b.

The woven layer 200 of FIG. 2 is one example of the type and configuration of weave that may be used in an embodiment. Other types of weaves known to those skilled in the art may be utilized. Also, various parameters of the weaves may be altered to achieve different weave characteristics. For example, the distance between fibers, such as the distance between fibers 202a and 202c may be varied to achieve various weave densities. Other woven layer 200 characteristics, such as thickness, may be achieved by altering fiber diameters and/or the configuration of the weave. All of the fibers of the woven layer 200 may be of the same diameter or the fibers may comprise a plurality of different diameters.

The woven layer 200 also includes void space. Void space is generally any space within the plane of the weave that is not occupied by any of the fibers that make up the woven layer 200. For example, the space 204 between fibers 202a, 202b, 202c, and 202d is part of the void space defined by the woven layer 200.

Figure 3:
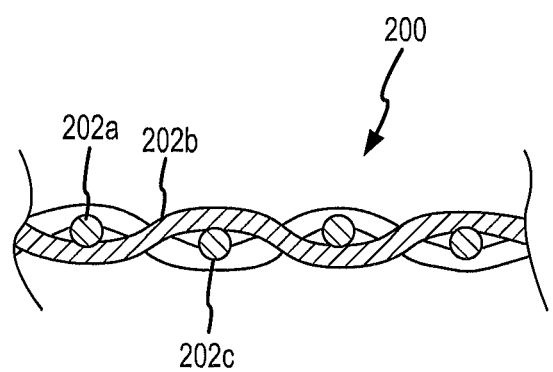
FIG. 3 is a cross sectional view of the woven layer of fibers of FIG. 2.

FIG. 3 is a cross sectional view of the exemplary woven layer 200 along section line A-A of FIG. 2. FIG. 3 shows the serpentine arrangement where individual fibers, such as fiber 202b, alternate position relative to other fibers of the weave.

The individual fibers of the woven layer 200, such as fiber 202b, may comprise a polymer. The polymer may be configured so that the fibers have a predeterminable porosity. Porosity is a measure of the interstitial space in a material. The interstitial space may be space within the polymer that does not contain the polymer. Porosity may be expressed as the proportion of the volume of the interstitial space in the material to the total volume of the material. Accordingly, the porosity will be between zero and one and may be given as a percentage. A value of zero would indicate no porosity. The interstitial space may contain air, water or any other substance. The interstitial space may contain a vacuum. For example, the porosity of the fibers of the woven layer 200 may be less than 85 percent.

In an embodiment, the individual fibers may be comprised of porous polymer, such as porous PTFE, porous urethane, porous polystyrene, porous silicone, porous fluoropolymer, porous polyolefin or a combination thereof. Porous polyolefin may, for example, be in the form of porous polyethylene, porous polypropylene, or a combination thereof. Porous polyethylene, porous polypropylene, and porous PTFE may be open-celled. Porous urethane, porous silicone, porous fluoropolymer, and porous polystyrene may be close-celled. In an embodiment, the individual fibers may be composed of a single type of porous polymer. In an embodiment comprising porous PTFE, the porous PTFE may, for example, have a microstructure similar to as described in U.S. Pat. No. 4,187,390 to Gore, the entirety of which is hereby incorporated by reference. In an embodiment comprising porous PTFE, the porous PTFE may, for example, have a microstructure similar to as described in U.S. Pat. No. 5,476,598 to Bacino, the entirety of which is hereby incorporated by reference.

The porosity may affect the acoustic attenuation properties of the porous polymer. For example, as the porosity is increased, the amount of captured air, which is a poor conductor of acoustic energy, may also increase, resulting in an aggregate material with exceptional acoustic attenuation properties. Porous polymers may be operable to attenuate acoustic energy having a frequency between 100 kHz and 100 MHz. For example, porous PTFE may have acoustic attenuation capabilities greater than 50 dB/cm at 1 MHz. In fact, porous PTFE may have acoustic attenuation capabilities greater than 10,000 dB/cm at 1 MHz. By comparison, silicone RTV may have an acoustic attenuation of less than 5 dB/cm at 1 MHz.

Figure 4:
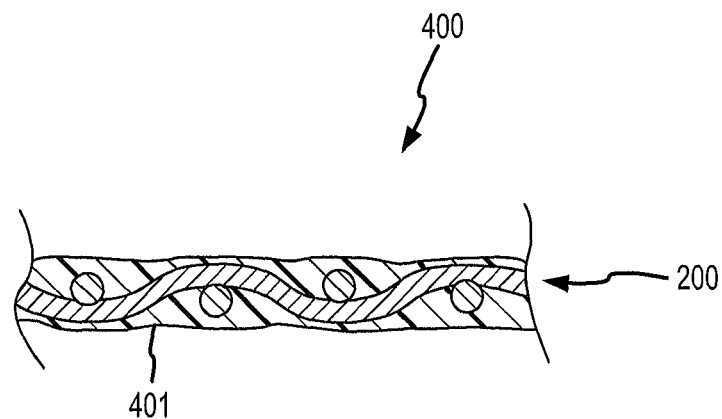
FIG. 4 is a cross sectional view of the woven layer of fibers of FIG. 2 with a filler material disposed within the void space between fibers.

FIG. 4 is a cross sectional view of the woven layer 200 in the same orientation as illustrated in FIG. 3 with a filler material 401 disposed within the void space between fibers. As illustrated in FIG. 4, the filler material 401 may fill the void space between individual fibers and also encapsulate the fibers. In such a configuration, the filler material 401 may perform several functions.

One such function may be to provide mechanical support for the porous fibers of the woven layer 200. In this regard, the filler material 401 may provide mechanical support for the woven layer 200 resulting in an encapsulated woven layer 400 that possesses a higher crush resistance than the woven layer 200 alone.

The filler material 401 may also encapsulate the air or other gasses trapped within the porosity of individual fibers of the woven layer 200. In this regard, the filler material 401 may surround and seal the individual fibers so that the air or other gasses trapped within the individual fibers cannot escape to the surrounding areas. Similarly, gasses or liquids outside of the encapsulated woven layer 400 may be prevented from entering the pores of the individual fibers of the woven layer 200.

In embodiments where the polymer is an open-celled polymer, the filler material 401 may surround the individual fibers of the woven layer 200 without significantly penetrating into the fibers. Alternatively, the filler material 401 may partially imbibe (e.g., partially soak into) the individual fibers of the woven layer 200. Such partial imbibing may result in increased mechanical strength. The portions of the individual fibers of the woven layer 200 not filled with the filler material 401 may contain, for example, entrained air. Accordingly, acoustic attenuation properties associated with the interstitial spaces of the individual fibers of the woven layer 200 may be retained after the individual fibers of the woven layer 200 have been surrounded by the filler material 401. With respect to open-celled polymers where partial imbibing is present, three distinct regions may be present. The first region may be the porous polymer where no filler material is present. The second region may be where the filler material has filled the interstitial regions of the porous polymer. The third region may be a layer consisting of the filler material outside of the porous polymer.

In embodiments where the polymer is a close-celled polymer, the filler material 401 may partially fill surface irregularities of the individual fibers of the woven layer 200. Such surface filling may promote bonding between the individual fibers of the woven layer 200 and the filler material 401.

As will be appreciated, by varying such parameters as, for example, the porosity of the polymer used in the individual fibers, the size of the individual fibers, the spacing between individual fibers within the woven layer 200, the degree to which the filler material 401 imbibes into the individual fibers (e.g., when the porous polymer is open-celled), and the amount of filler material 401 used to encapsulate the woven layer 200, various mechanical and acoustical properties of the encapsulated woven layer 400 may be achieved. In an embodiment, the filler material 401 may be a thermoplastic and/or thermoset material. The filler material 401 may comprise THV, FEP, PTFE, PES, EFEP, PET, PEEK, PEI, PC, LCP, or a combination thereof. An exemplary thermoplastic material is THV, such as Dyneon™ THV marketed by 3M, St. Paul. Minn., U.S.A. In an exemplary embodiment including porous PTFE and THV, the combination of PTFE and THV may have a benefit in that the acoustic impedance and acoustic propagation velocity of the two materials are similar enough not to cause significant reflections at the interface between the two materials.

Figure 5:
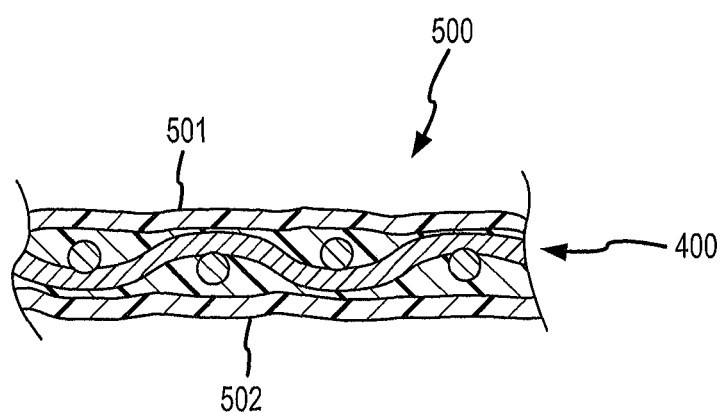
FIG. 5 is a cross sectional view of the woven layer of fibers of FIG. 2 with a filler material disposed within the void space between fibers and membranes disposed on the top and bottom of the woven layer.

Turning to FIG. 5, an acoustic attenuation material member 500 may comprise a first additional layer 501 and a second additional layer 502 that may be interconnected to the encapsulated woven layer 400. In an alternate embodiment, the acoustic attenuation material member 500 may contain the single additional layer 501 but not the second additional layer 502. The additional layers 501 and 502 may comprise a polymer with a predeterminable level of porosity. The additional layers 501 and 502 may provide additional acoustic attenuation capabilities and provide additional mechanical strength. An example of a material that comprises a woven layer of porous PTFE fibers encapsulated in THV is Tenara manufactured by W. L. Gore & Associates, Inc., Newark, Del., U.S.A.

Figure 6:
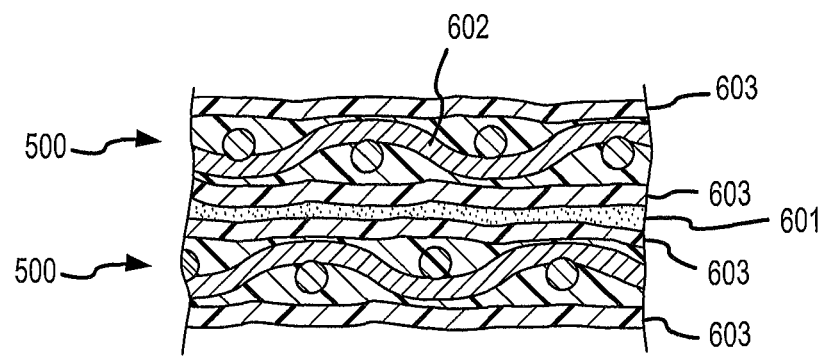
FIG. 6 is a cross sectional view of two layers of materials, similar to as shown in FIG. 5, bonded together.

FIG. 6 is a cross sectional view of an embodiment where two layers of the acoustic attenuation material member 500, as illustrated in FIG. 5, are bonded together with a layer of binding material 601. The layer of binding material 601 may be comprised of an adhesive polymer such as, for example, epoxy. In an exemplary implementation of the embodiment illustrated in FIG. 6, each of the acoustic attenuation material members 500 comprised porous PTFE fibers (e.g., fiber 602) and porous PTFE additional layers 603. The layer of bonding material 601 was less than 0.025 mm in thickness and each of the acoustic attenuation material members 500 was about 0.38 mm thick. Thicker layers of bonding material may be used, such as, for example, 0.05 mm.

Figure 7:
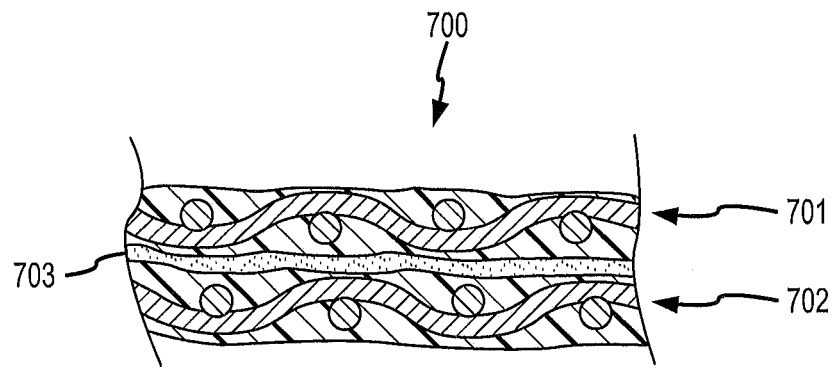
FIG. 7 is a cross sectional view of two layers of materials as shown in FIG. 4 bonded together.

In an embodiment of an acoustic attenuation material illustrated in FIG. 7, two sheets 701, 702, each similar to the encapsulated woven layer 400 of FIG. 4 and including an encapsulated layer of woven porous polymer fibers, may be bonded together with a bonding layer 703 (e.g., epoxy) to form an acoustic attenuation material 700 that remains flexible and has particular acoustic attenuation properties.

Materials as described that include at least one layer comprising a woven layer of polymer fibers with interstitial space may be used in a variety of acoustic attenuation applications. Such materials may be used in ultrasound probes such as the above-described ultrasound probe of FIG. 1. The materials may also be used in other acoustic attenuation applications.

Figure 8A:
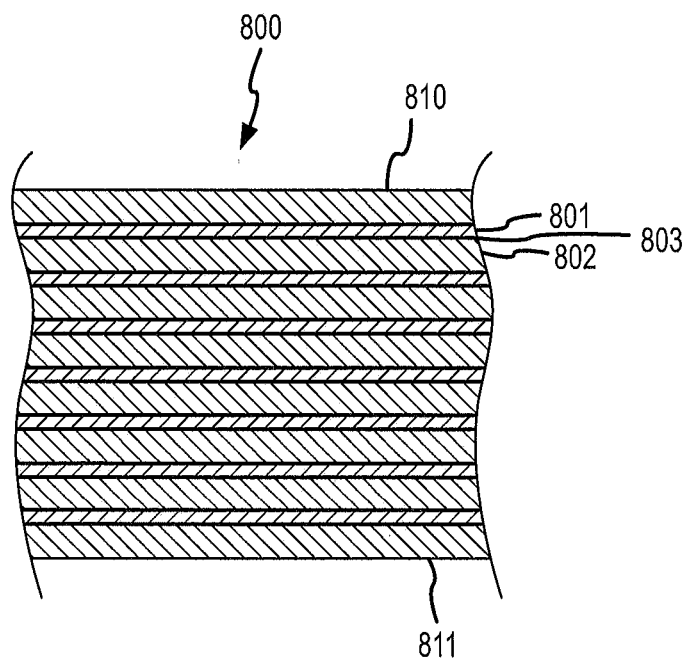
FIG. 8A is a cross sectional view of a material that comprises a plurality of layers of porous polymer sheets interleaved with a plurality of sheets of support material.

FIG. 8A is a cross-sectional view of an acoustic attenuation material 800 that includes a plurality of porous-polymer sheets 801 (e.g., membranes) interleaved with a plurality of sheets of support material 802 (e.g., membranes and/or films). Such an acoustic attenuation material 800 may be used, for example, for attenuating acoustic energy, including attenuating ultrasonic energy in ultrasound probes. The porous polymer of the porous-polymer sheets 801 may be one or more of the previously discussed porous polymers. The porous polymer sheets may be comprised of a non-woven porous polymer. The sheets of support material 802 may, for example, be comprised of a ceramic material, polymer, metal, or a combination thereof. In embodiments where the sheets of support material 802 comprise polymer, the polymer may be a thermoset or a thermoplastic. For example, the polymer may be epoxy or fluoropolymer.

The sheets of support material 802 may be more rigid than the porous-polymer sheets 801. In this regard, in the acoustic attenuation material 800, the porous-polymer sheets 801 may provide substantial acoustic attenuation and the sheets of support material 802 may provide for greater rigidity than would be achievable with the porous-polymer sheets 801 alone. In this regard, the support material 802 may have a greater resistance to crushing and a greater flexural modulus than the porous-polymer sheets 801. For example, the flexural modulus of the support material 802 may be at least twice that of the porous-polymer sheets 801. Also for example, the flexural modulus of the porous-polymer sheets 801 may be less than 20 MPa while the net flexural modulus of acoustic attenuation material 800 may be greater than 40 MPa.

The individual sheets of the acoustic attenuation material 800 may be individually constructed and then laminated together to form the acoustic attenuation material 800. The layers of the laminated structure may be bonded together using an adhesive. The layers of the laminated structure may be bonded together by processing the laminate so that some imbibing of the sheets of support material 802 into the porous-polymer sheets 801 occurs.

The layers of the laminated structure may be bonded together using layers of adhesive disposed on a carrier. The adhesive may be pressure sensitive, such as for example, acrylic based pressure sensitive adhesive. For example, a thin layer of double-sided tape 803 may be disposed between adjacent layers of porous-polymer sheets 801 and support material 802. Other methods of laminating sheets known to those skilled in the art may be employed.

The thicknesses of the sheets of support material 802 and the porous-polymer sheets 801 may be varied to achieve various mechanical and acoustic properties. For example, as shown in FIG. 8A, the thicknesses of the porous-polymer sheets 801 may be less than the thickness of the sheets of support material 802. In other embodiments, the sheets may be of equal thickness or the porous-polymer sheets 801 may be thicker than the sheets of support material 802.

In an embodiment, each porous-polymer sheet 801 may have a thickness less than 800 microns, and each sheet of support material 802 may have a thickness less than 500 microns. For example, each porous-polymer sheet 801 may have a thickness between 1 and 800 microns, and each sheet of support material 802 may have a thickness between 1 and 500 microns. In a particular exemplary embodiment, each porous-polymer sheet 801 may be about 30 microns thick and each sheet of support material 802 may be about 25 microns thick.

Figure 8B:
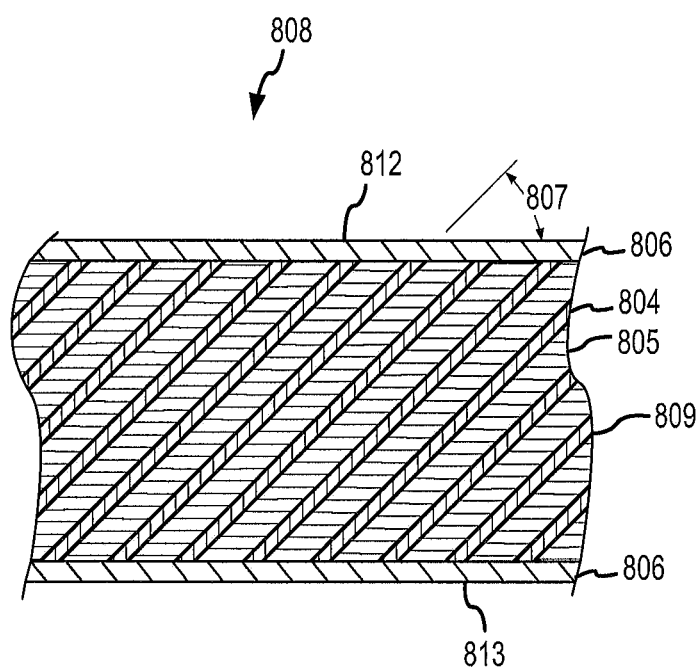
FIG. 8B is a cross sectional view of a material that comprises a plurality of layers of porous polymer sheets interleaved with a plurality of sheets of support material.

The acoustic attenuation material 800 illustrated in FIG. 8A shows a configuration where individual layers are in the same orientation as the overall structure. FIG. 8B is a cross-sectional view of an acoustic attenuation material 808 that includes a plurality of porous-polymer sheets 804 interleaved with a plurality of sheets of a support material 805. In the embodiment illustrated in FIG. 8B, the orientation of the individual layers 804, 805 is oriented at an angle 807 with respect to the orientation of the overall structure of the acoustic attenuation material 808. The angle 807 may be varied to achieve various acoustic and mechanical properties. Optional sealing layers 806 may be added to the top and/or bottom of the acoustic attenuation material 808 to prevent exposure of the edges of the porous-polymer sheets 804 and/or sheets of support material 805 to the surrounding environment. The quantity of layers present in the acoustic attenuation materials 800 and 808 may be varied from that illustrated in FIGS. 8A and 8B.

The configuration of FIG. 8A is such that a sound beam traveling from a first side 810 of the acoustic attenuation material 800 to a second side of the acoustic attenuation material 811 must pass through a plurality of layers of the porous-polymer sheets such as the porous-polymer sheets 801. The angle 807 of the configuration of FIG. 8B, along with the orientation of the overall structure of the acoustic attenuation material 808, may be chosen such that a sound beam traveling from a first side 812 of the acoustic attenuation material 808 to a second side 813 of the acoustic attenuation material 808 must pass through a plurality of layers of the porous-polymer sheets such as porous-polymer sheet 804.

Materials as described with reference to FIGS. 8A and 8B that include a plurality of porous-polymer sheets interleaved with a plurality of sheets of support material may be used in a variety of acoustic attenuation applications. Such materials may possess a net acoustic attenuation of at least 25 dB/cm at 1 MHz and may be operable to attenuate acoustic energy having a frequency between 100 kHz and 100 MHz. Such materials may be used in ultrasound probes such as the above-described ultrasound probe of FIG. 1. The materials may also be used in other acoustic attenuation applications.

Figure 9:
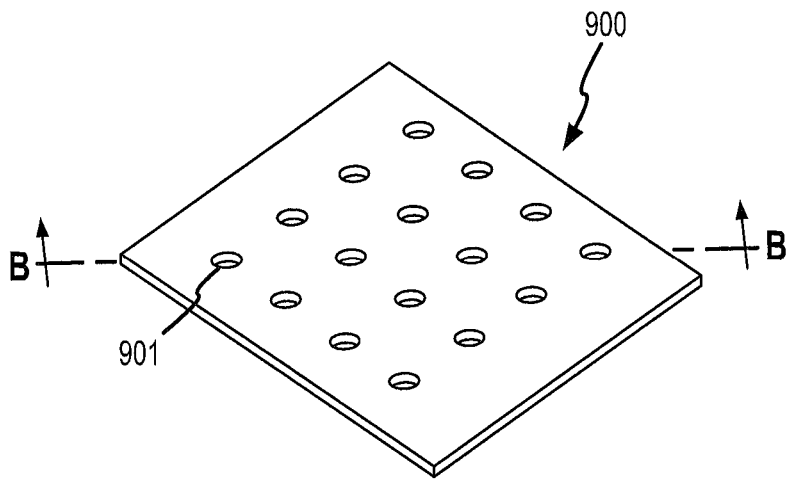
FIG. 9 is an isometric view of a section of an embodiment of a sheet of porous polymer comprising multiple through holes.

FIG. 9 is an isometric view of a section of an acoustic attenuation material that includes a sheet 900 comprised of a porous polymer comprising multiple through holes, such as through hole 901. In an exemplary embodiment, the sheet 900 may be between 1 and 200 microns thick. The porous polymer of the sheet 900 may be one or more of the previously discussed polymers. In an embodiment, the sheet 900 may be constructed of porous PTFE, and/or other porous polymers (e.g., urethane, silicone, fluoropolymer, polystyrene and polyolefin). The sheet 900 may be comprised of a non-woven porous polymer.

Figure 10:
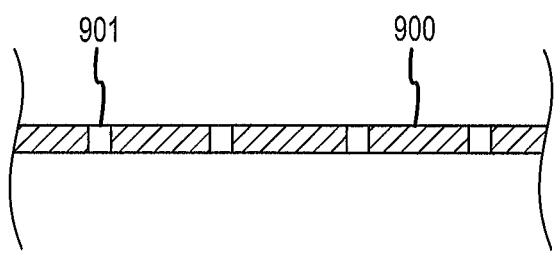
FIG. 10 is a cross sectional view of the sheet of FIG. 9.

The sizes of the holes (e.g., the area or diameter of the holes), the number of holes, and the pattern of holes may all be varied to achieve particular material properties as discussed below. FIG. 10 is a cross sectional view of the sheet 900 of FIG. 9 along section line B-B, The holes may be created by any appropriate means known to those skilled in the art, including for example, laser drilling. The holes may be uniformly or non-uniformly distributed. The holes may all be the same size or the sizes of individual holes may vary.

Figure 11:
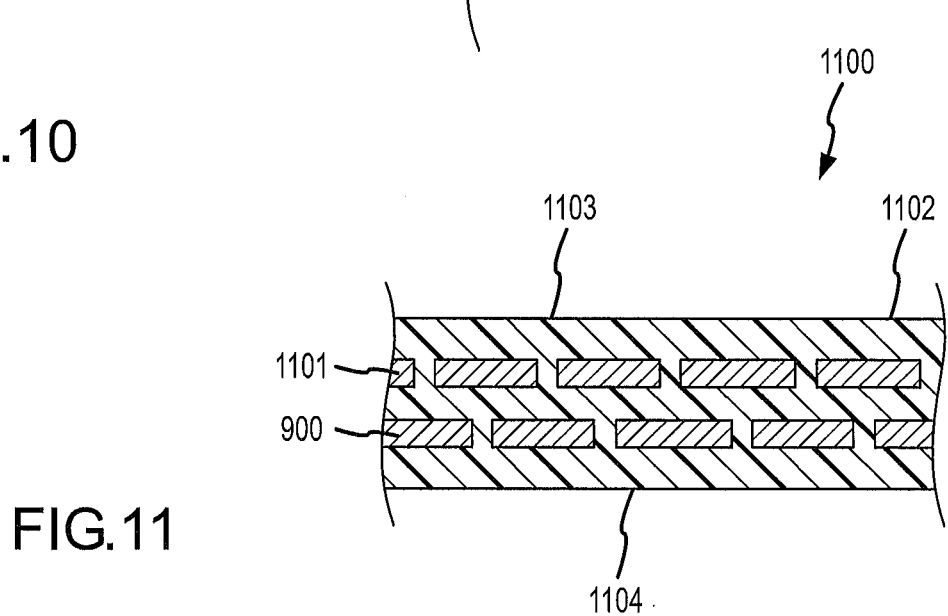
FIG. 11 is a cross sectional view of multiple layers of the sheet of FIG. 9 interleaved with multiple layers of support material.

FIG. 11 is a cross sectional view of an embodiment of a rigid composite material 1100. The rigid composite material 1100 includes a plurality of layers of porous-polymer sheets such as the sheet 900 of acoustic attenuation material and an additional sheet 1101 of acoustic attenuation material. The additional sheet 1101 may be constructed of the same material and may also have the same through hole characteristics as the sheet 900. As illustrated in FIG. 11, the porous-polymer sheets may be interleaved with layers of a support material 1102. The layers of support material 1102 may also occupy at least a portion of the through holes of the porous-polymer sheets 900, 1101. In this regard, the layers of support material 1102 may form a three-dimensionally interconnected rigid matrix. The thickness of the layers of support material 1102 between the porous-polymer sheets 900, 1101 may, for example, be between 1 and 200 microns thick.

The combination of layers of support material 1102 interleaved with layers of acoustic attenuation material provides for a composite material 1100 that possesses exceptional acoustic attenuation and mechanical properties. In this regard, the layers of support material 1102, which may, for example, comprise epoxy, THV, FEP, PES, EFEP, PTFE, PET, PEEK, PEI, PC, LCP or a combination thereof, may have a greater resistance to crushing and a greater flexural modulus than the porous-polymer sheets 900, 1101. For example, the flexural modulus of the layers of support material 1102 may be at least twice that of the porous-polymer sheets 900, 1101. Also for example, the flexural modulus of the porous-polymer sheets 900, 1101 may be less than 20 MPa while the net flexural modulus of composite material 1100 may be greater than 40 MPa.

Thus, the composite material 1100 may gain mechanical strength from the layers of support material 1102 while gaining acoustic attenuation properties from the porous-polymer sheets 900, 1101. The composite material may possess a net acoustic attenuation of at least 25 dB/cm at 1 MHz and may be operable to attenuate acoustic energy having a frequency between 100 kHz and 100 MHz.

The mechanical and acoustical properties of the composite material 1100 may be varied by varying the thicknesses of the different layers and the configurations of the holes in the porous-polymer sheets. For example, as shown in FIG. 11, the holes in the two sheets 900, 1101 are not aligned. In general, the porous-polymer sheets 900, 1101 will have a significantly higher rate of acoustic attenuation than the layers of support material 1102. Accordingly, acoustic energy passing through the rigid composite material 1100 will be transmitted primarily through the structure of the layers of support material 1102. By staggering the holes of the porous-polymer sheets 900, 1101, the acoustic energy traveling through the layers of support material 1102 is forced to follow a serpentine path. In this regard, any sound beam traveling from a top surface 1103, through the composite material 1100 to a bottom surface 1104, must pass through at least a portion of the porous-polymer sheets 900, 1101. This will tend to attenuate the acoustic energy to a greater degree than what would occur if the holes of the porous-polymer sheets 900, 1101 were in a line and the acoustic energy traveling through the layers of support material 1102 were able to follow a straight-line path through the composite material 1100.

Similar to the alignment of the holes of the porous-polymer sheets, the size and quantity of holes may be varied to balance desired acoustic attenuation properties and desired mechanical properties. For example, in general larger through holes may result in a more rigid and stronger composite material 1100. Larger through holes or increased number of through holes may also result in a larger pathway for acoustic energy to travel through the rigid composite material 1100, which may result in a more rigid, stronger composite material 1100 with lower overall acoustic attenuation.

Additionally, and similar to as discussed above, some imbibing of the epoxy into the layers of porous-polymer may occur where open-celled polymer is used. Substantially no imbibing may occur where the pore size of an open-celled polymer is below a predetermined amount or where a close-celled polymer is used. Where imbibing does occur, it may have a similar effect as reducing the thickness of the porous-polymer layers and/or increasing the size of the through holes of the porous-polymer layers 900, 1101.

Moreover, in general, regions where support material has imbibed into a portion of the porosity of a porous-polymer layer may be significantly stiffer then regions of the porous-polymer layer free of the support material. For example, a region where support material has imbibed into a portion of the porosity of a porous-polymer layer may have a flexural modulus greater than twice that of a region of the porous-polymer layer free of support material.

The degree of imbibing may be affected by processing and handling. For example, in embodiments that include porous PTFE, wetting the porous PTFE with a solvent prior to contact with the layers of support material 1102 during the manufacture of the composite material 1100 may increase the degree of imbibing of the support material into the porous PTFE. Additionally, any compressive forces applied to the composite material 1100 during or after manufacture may cause the layers of support material 1102 to imbibe into the porous-polymer layers 900, 1101. Compressive forces on the composite material 1100 may also crush (e.g., permanently compress) the porous-polymer layers 900, 1101.

The composite material 1100 illustrated in FIG. 11 includes two porous-polymer layers 900, 1101. Other embodiments may include a single porous-polymer layer or more than two porous-polymer layers. For example, an embodiment of an acoustic attenuation material was constructed using three porous-PTFE layers interleaved with layers of epoxy. A plurality of holes averaging about 0.14 mm in diameter and encompassing about 10.7 percent of the total surface area of the porous-PTFE layers were drilled into each of the PTFE layers. In one sample, the holes of the individual porous-PTFE layers were arranged with a high degree of alignment. The acoustic attenuation of that sample was measured to be 375 dB/cm at 1 MHz. In another sample, the holes of the individual porous-PTFE layers were arranged with a relatively low degree of alignment. The acoustic attenuation of the low degree of alignment sample was measured to be 431 dB/cm at 1 MHz.

Another embodiment was constructed using two porous-PTFE layers interleaved with layers of epoxy. The porous-PTFE layers included a plurality of holes. The embodiment showed no plastic deformation when compressed at 50 psi. A similar embodiment without the plurality of holes in the porous-PTFE layers may show plastic deformation of about 3 percent when compressed at 50 psi.

Blind holes may be substituted for the through holes described above, such as through hole 901. Such a configuration eliminates a continuous support material acoustic path through the composite material 1100.

Materials as described that include at least one sheet of a porous polymer that includes holes (e.g., through holes) may be used in a variety of acoustic attenuation applications. Such materials may be used in ultrasound probes such as the above-described ultrasound probe of FIG. 1. The materials may also be used in other acoustic attenuation applications. Indeed, such materials may be used in a wide variety of applications where it is desired to attenuate acoustic energy.

Each of the acoustic attenuation materials described above may be produced in master sheets that are larger than the size needed for a particular application. For example, a master sheet of acoustic attenuation material may be produced for use as backing material in ultrasonic transducers that includes enough material for a plurality of individual ultrasonic transducer systems. The master sheet may, for example, be separated into individual sections for use in individual ultrasonic transducer systems. The process may also include a step where exposed edges of the individual sections are sealed with a sealing material (e.g., epoxy and/or thermoplastic fluoropolymer).

In embodiments where individual sections of acoustic attenuation material are manufactured (e.g., where no master sheets are produced), the process may include a step where exposed edges of acoustic attenuation material are sealed with a sealing material (e.g., epoxy and/or thermoplastic fluoropolymer).

In each of the acoustic attenuation materials described above, the porous polymer may have significantly greater acoustic attenuation capabilities than the material used to provide support. For example, the acoustic attenuation capabilities of the porous polymer may be more than twice that of the support material. Additionally, the support material may be significantly more rigid (e.g., possess a greater stiffness) than the porous polymer. For example, the support material may have a flexural modulus twice that of the porous polymer. Moreover, the porous polymer may have a porosity of at least 5 percent. For example, the porous polymer may have a porosity of between 5 and 85 percent.

The above-described materials may, for example, be utilized in systems where it is desired to control acoustic energy. Additionally, due to the relatively high attenuation per unit thickness of the above-described materials, greater attenuation can be achieved for a particular thickness of attenuation material or alternatively, a desired amount of attenuation can be used with relatively less attenuation material. The latter capability is particularly advantageous in applications where miniaturization is desired. In particular, ultrasound probes, an example of which was previously discussed with reference to FIG. 1, generally utilize acoustic attenuation material to control the acoustic energy generated by one or more active (e.g., piezoelectric) elements. The use of the above-described materials in ultrasonic transducers may, for example, enable better performing probes of the same size as current probes and/or smaller transducer probes.

Figure 12:
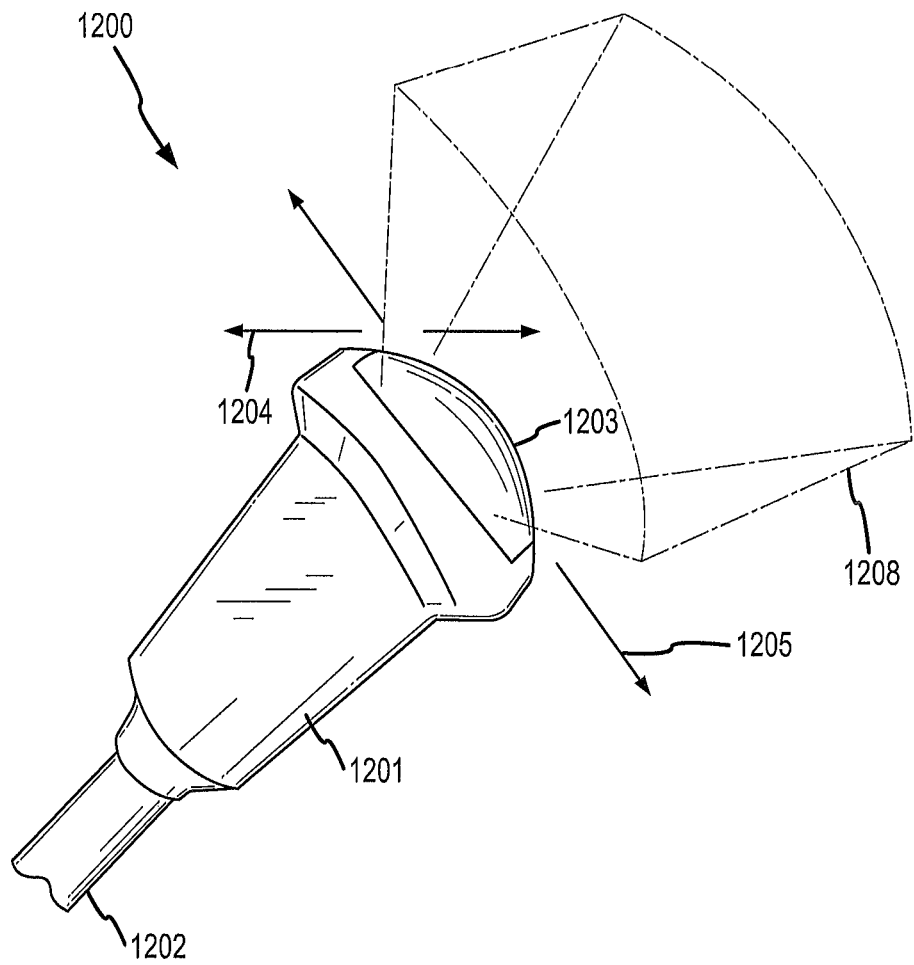
FIG. 12 is an isometric view of an embodiment of an ultrasound probe assembly.

FIG. 12 illustrates a perspective view of an ultrasound probe assembly 1200. The probe assembly 1200 includes a housing 1201 and a cable 1202. The cable 1202 is interconnected to an ultrasound imaging apparatus (not shown). Generally, the probe assembly 1200 includes a plurality of ultrasonic transducers contained within the housing 1201 and operable to transmit ultrasonic energy through a probe assembly face 1203 along one end of the probe assembly 1200. The ultrasonic energy, in the form of acoustic waves, may be directed through the outer surface of a patient and into the internal structure of the patient. The acoustic waves may interact with and reflect off of various internal features. These reflections may then be detected by the probe assembly 1200 and displayed as images of the internal structure of the patient by the ultrasound imaging apparatus.

The probe assembly 1200 may be operable to scan an imaging volume 1208. This may be accomplished by mounting a one-dimensional transducer array on a movable member. Generally, one-dimensional transducer arrays include a single row containing a plurality of transducer elements along a longitudinal axis 1205. Through electronic control, a beam of acoustic energy may be swept along the longitudinal axis 1205. Some of the acoustic energy is reflected back to the transducer array where it is converted by the transducer array from acoustic energy to electrical signals. These electrical signals may then be converted into a two-dimensional image of the area swept by the acoustic energy. The probe assembly 1200 may contain a one-dimensional transducer array that may be mechanically swept (e.g., rotated) along an elevation axis 1204. Thus, through a combination of electronic sweeping along a longitudinal axis 1205 and mechanical sweeping of the transducer array along an elevation axis 1204, a beam of acoustic energy may be swept through the imaging volume 1208. Energy reflected back to the transducer array may be converted into a three-dimensional image of the imaging volume 1208.

The transducer array in probe assembly 1200 may be a two-dimensional array that may be mechanically swept (e.g., rotated) along an elevation axis 1204. The dimension of the array perpendicular to the axis of rotation (e.g., the elevation axis 1204) may be utilized to further control the transmitted acoustic energy. For example, transducers along the elevation axis 1204 may be used to shape the acoustic energy to reduce side lobes and improve focus along the elevation axis 1204.

Figure 13:
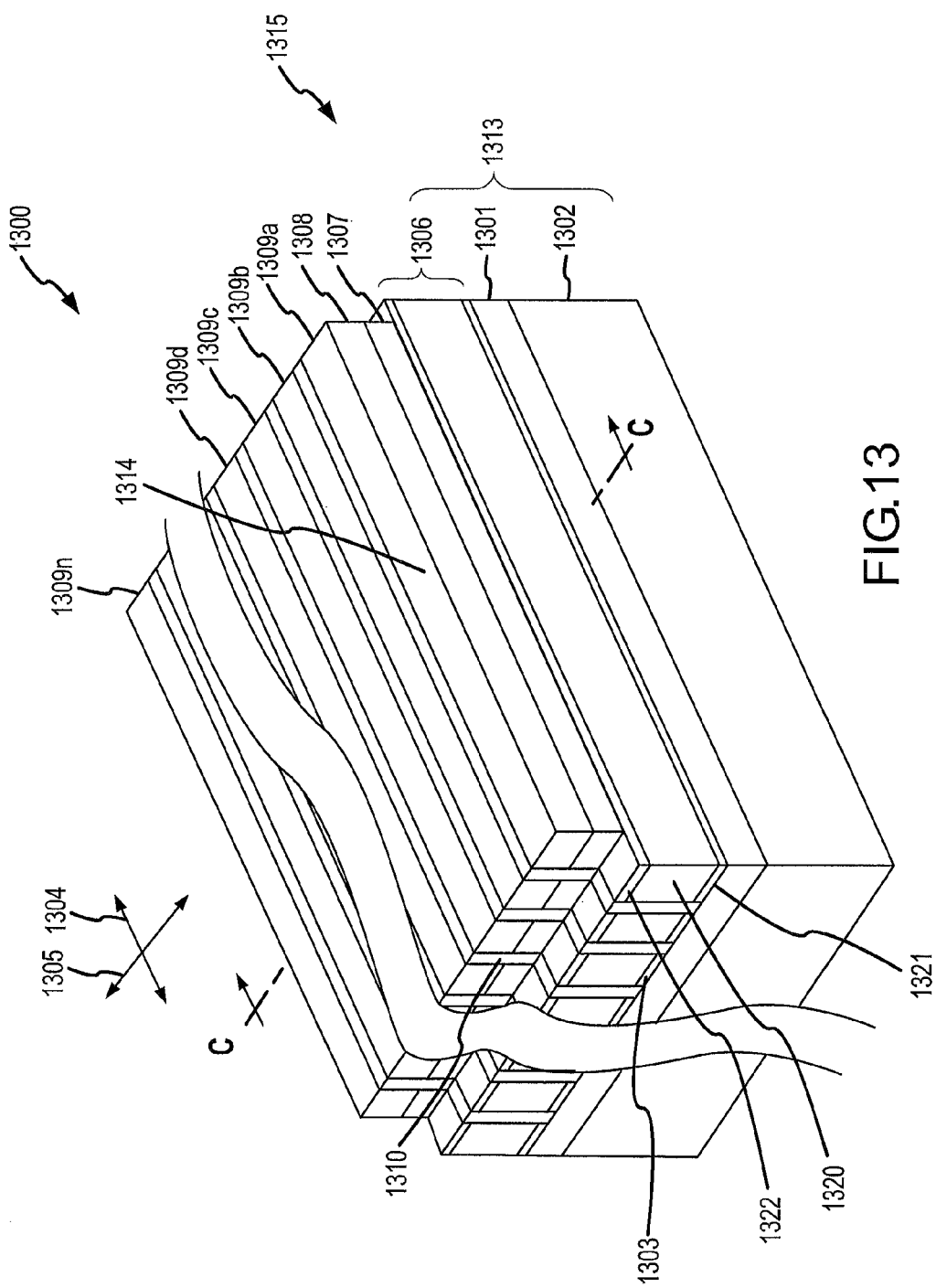
FIG. 13 is a schematic view of a portion of the ultrasonic transducer of FIG. 12.

Turning to FIG. 13, a cross-sectional schematic view of a one-dimensional ultrasonic transducer system 1300 is presented. The ultrasonic transducer system 1300 has a longitudinal axis 1305 and an elevation axis 1304, which, for example, are similar to the longitudinal axis 1205 and elevation axis 1204, respectively, of the probe assembly of FIG. 12. The ultrasonic transducer system 1300 may be operable to transmit and/or receive ultrasonic signals.

Generally, as known to those skilled in the art, a transducer 1315 (comprising an active layer such as piezoelectric layer 1306 and any optional matching layer attached thereto described below) may be divided into a predetermined number of discrete sections (for example, sections 1309*a* through 1309*n*, where n represents the predetermined number of discreet sections) along the longitudinal axis 1305. Each of these discrete sections may be a transducer element (e.g., discrete section 1309*a* may be a transducer element). The discrete sections may be electrically interconnected so that two or more of the discrete sections operate as a single transducer element (e.g., discrete sections 1309*a* and 1309*b* may be electrically interconnected and function as a single transducer element). A backing 1313 may also be present.

FIG. 13 shows the ultrasonic transducer system 1300 as being straight along the longitudinal axis 1305. The ultrasonic transducer system 1300 may be curved along the longitudinal axis 1305. This curvature may, for example, be achieved by placing individual planar transducer elements at angles to each other along the longitudinal axis 1305. FIG. 13 also shows the individual transducer elements of the ultrasonic transducer system 1300 as planar along the elevation axis 1304. In an alternative configuration, the individual transducer elements of the ultrasonic transducer system 1300 may be curved along the elevation axis 1304.

The transducer 1315 may include a piezoelectric layer 1306. The piezoelectric layer 1306 may include a layer of piezoelectric material 1320, a first electrode layer 1321 and a second electrode layer 1322. The layer of piezoelectric material 1320 may be comprised of a ceramic-based material (e.g., lead zirconate titanate (PZT)). The first electrode layer 1321 may be comprised of one or more layers of electrically conductive material. Similarly, the second electrode layer 1322 may be comprised of one or more layers of electrically conductive material. The portion of the first electrode layer 1321 connected to each individual transducer element may serve as the signal electrode for that individual transducer element. Similarly, the portion of the second electrode layer 1322 connected to each individual transducer element may serve as the ground electrode for that individual transducer element.

Generally, the signal electrodes and ground electrodes are arranged as illustrated in FIG. 13 with the ground electrode on the side of the piezoelectric material 1320 that faces the region to be imaged. The position of the signal and ground electrodes may be reversed. In such embodiments, it may be necessary to provide an additional grounding layer to shield the signal layer. The ground electrodes may be individual electrodes as illustrated in FIG. 13 or may be one continuous layer of grounding material situated over each of the individual transducer elements. The individual transducer element electrodes may be interconnected to electronic circuitry, which may provide for acoustic wave generation and sensing.

Optional acoustic matching layers may be interconnected to the piezoelectric layer 1306. The ultrasonic transducer system 1300 of FIG. 13 shows a first optional matching layer 1307 and a second optional matching layer 1308 interconnected to the piezoelectric layer 1306. The presence and number of optional matching layers may vary from the configuration illustrated in FIG. 13. The transducer 1315 comprises the piezoelectric layer 1306, along with any optional matching layers attached thereto.

The piezoelectric layer 1306 may be a mechanically active layer operable to convert electrical energy to mechanical energy and mechanical energy into electrical energy. As previously described, the piezoelectric layer 1306 may be comprised of a layer of PZT material sandwiched between ground and signal electrodes. A variety of components and materials able to generate acoustic signals may be substituted for at least a portion of the piezoelectric layer 1306. Such components and materials include ceramic materials, ferroelectric materials, composite materials, capacitor micromachined ultrasound transducers (CMUTs), piezoelectric micromachined ultrasound transducers (PMUTs), and any combination thereof. Regardless of the specific components, electromechanical principle of operation or materials, the mechanically active layer may comprise a means of converting electrical energy to mechanical energy and mechanical energy into electrical energy, which has an acoustic face 1314 and a plurality of transducer elements that may be controlled individually. Generally, any system known to those skilled in the art for generating ultrasonic acoustic signals that may be used for imaging purposes may be utilized in the mechanically active layer.

Returning to FIG. 13, each individual discrete section may be separated from neighboring discrete sections by kerfs (e.g., kerf 1310 between discrete sections 1309c and 1309d) produced during the dicing of the transducer 1315. The kerfs may be filled with a filler material. Additionally, one or more acoustic lenses may be interconnected to the acoustic face 1314.

As the piezoelectric layer 1306 emits acoustic energy, some acoustic energy will pass into the backing 1313. Since such acoustic energy is not directed to the imaging volume 1208, it is desirable that this acoustic energy be attenuated. Attenuating this acoustic energy helps to reduce the amount of acoustic energy being reflected back into the piezoelectric layer 1306 through the back side of the piezoelectric layer 1306. Such reflected acoustic energy may interfere with the acoustic energy being reflected back to the piezoelectric 1306 from the imaging volume 1208, which may result in image degradation.

The backing 1313 may include an intermediate layer 1301. The intermediate layer 1301 may be comprised of material or materials known to those skilled in the art of ultrasonic transducer design, such as, for example epoxy, silicone rubber, tungsten, aluminum oxide, mica, microspheres, or a combination thereof. The backing 1313 may also include a second layer 1302. The second layer 1302 may be a highly attenuating material such as the materials previously described that include a woven layer of fibers made of porous-polymers (e.g., the fibers may be made of porous-PTFE). By way of example, the second layer 1302 may be composed of the acoustic attenuation materials described with respect to FIGS. 6 and/or 7.

Figure 14:
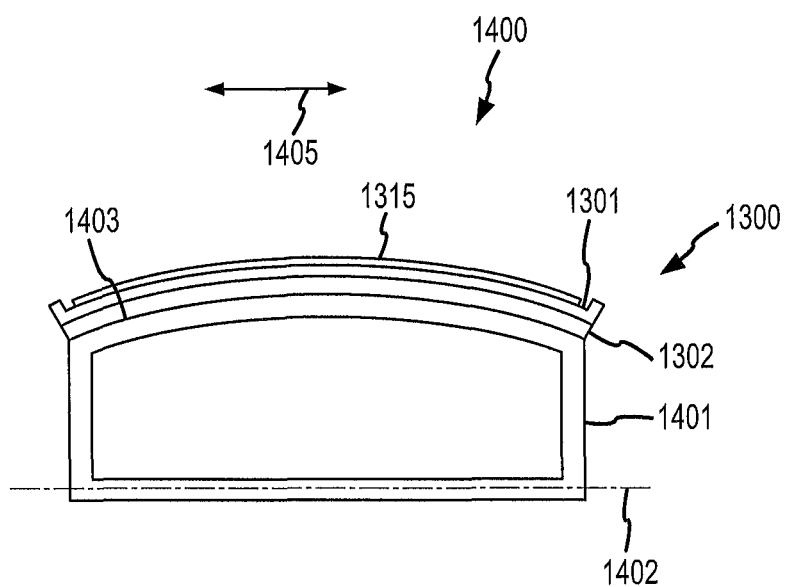
FIG. 14 illustrates an embodiment of an ultrasonic transducer attached to a frame.

FIG. 14 is an illustration of a transducer and frame assembly 1400. The transducer and frame assembly 1400 includes the ultrasonic transducer system 1300 of FIG. 13 mounted to a frame 1401. As described above with respect to FIG. 13, the ultrasonic transducer system 1300 may include the transducer array 1315, the intermediate layer 1301, and the second layer 1302. The transducer and frame assembly 1400 may, for example, be mounted within the probe assembly 1200 of FIG. 12. The transducer and frame assembly 1400 may be mounted so that it is rotatable about a frame rotation axis 1402. In such a system, and as previously described, an acoustic beam may be electronically steered along a longitudinal axis 1405 and mechanically steered by rotating the transducer and frame assembly 1400 about the frame rotation axis 1402. A motor or other device (not shown) may be used to rotate the transducer and frame assembly 1400 about the frame rotation axis 1402.

To acoustically couple the transducer array 1300 to the probe assembly face 1203 of FIG. 12, the transducer and frame assembly 1400 may be immersed in a fluid (e.g., a liquid). The fluid may be contained within the housing 1201 of the probe assembly 1200 of FIG. 12.

As noted above, the transducer and frame assembly 1400 may be rotated within the housing 1201 in order to achieve scanning of an acoustic beam along an elevation axis 1204. Furthermore, and as noted above, the transducer and frame assembly 1400 may be immersed in a liquid. In such a system, it may be beneficial to reduce the size and/or weight of the transducer and frame assembly 1400. By reducing the size of the transducer and frame assembly 1400, the resistance to movement of the transducer and frame assembly 1400 due to the fluid in which it is immersed may be reduced. By reducing the weight of the transducer and frame assembly 1400, the inertia of the transducer and frame assembly 1400 may be reduced. Reducing the resistance to movement and/or the inertia of the transducer frame assembly 1400 may yield, inter alia, increased positional accuracy, lower movement response time, and reduced motor power requirements.

Accordingly, the use of a backing that incorporates at least one woven layer of porous-polymer fibers, as described above, in place of traditional ultrasonic transducer backing material (e.g., silicone rubber) may provide weight and size reduction benefits. Similarly, if a traditional ultrasonic transducer backing material is replaced with a similarly sized backing that incorporates at least one woven layer of porous-polymer fibers, the acoustic attenuation of the backing may be enhanced.

Additionally, the flexibility of the above-described woven layers of porous-polymer fibers permits curved transducer arrays, such as the transducer array 1300 of FIG. 14, to be manufactured efficiently. For example, the transducer array 1300 of FIG. 14 may be initially manufactured as a flat transducer array. In this regard, a flat continuous layer of piezoelectric material may be interconnected to a backing that includes at least one woven layer of the porous polymer fibers. After the piezoelectric material is diced to form individual transducer array elements, this assembly may be interconnected to a curved surface, such as the curved surface 1403 of the frame 1401 of the transducer and frame assembly 1400. The kerfs produced as a result of the dicing process may then be filled.

Returning to FIG. 13, the first electrode layer 1321 and the second electrode layer 1322 may be electrically interconnected to the ultrasound imaging apparatus in a variety of ways. For example, the electrical interconnections to the first electrode layer 1321 of each individual transducer element (e.g., discrete sections 1309a through 1309n) may be achieved by electrically interconnecting to the first electrode layer 1321 along an the edge of the transducer 1315. For example, the first electrode layer 1321 of discrete section 1309c may be interconnected to at the exposed end 1303 of discrete section 1309c.

Figure 15:
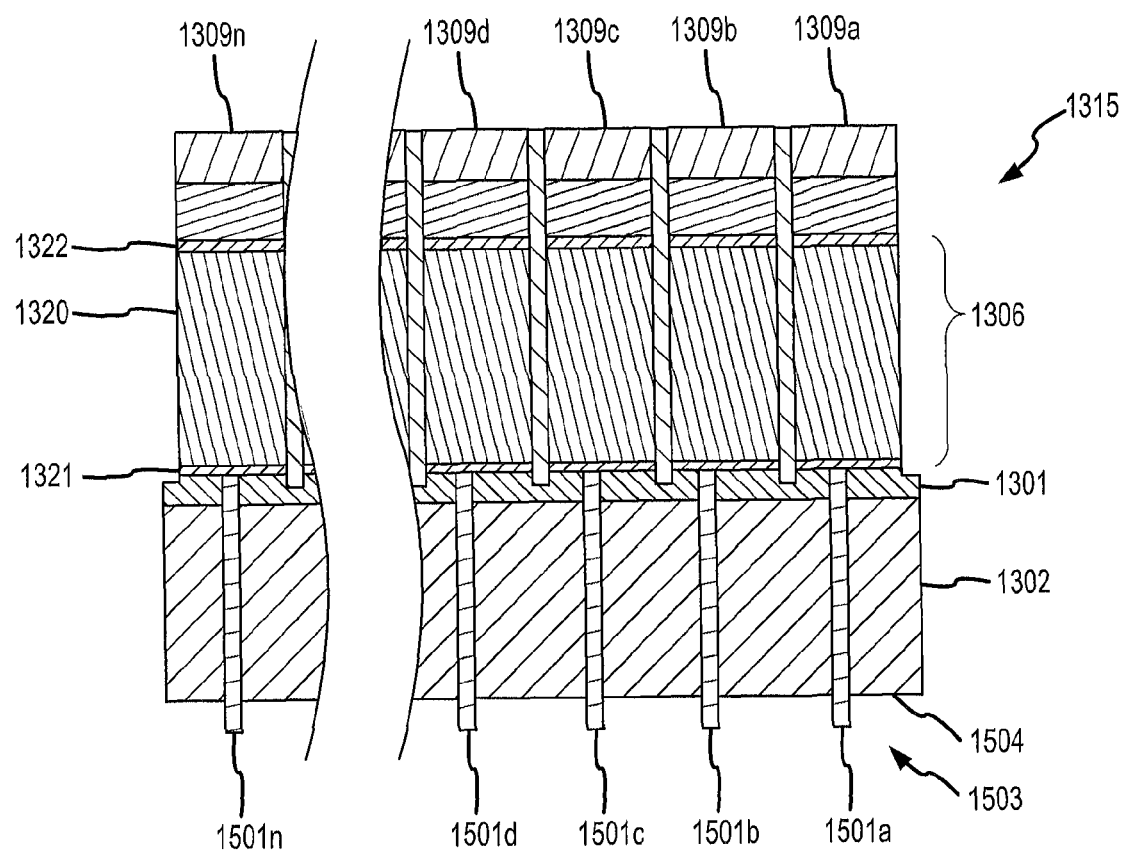
FIG. 15 is a cross sectional view of an embodiment of an ultrasonic transducer assembly.

FIG. 15 illustrates another method of electrically interconnecting the ultrasound imaging apparatus to the first electrode layer 1321 of the discrete sections of the transducer 1315. FIG. 15 is a cross-sectional view of the ultrasonic transducer system 1300 of FIG. 13 along section line C-C of FIG. 13 with the addition of a plurality of electrical interconnections 1501a through 1501n. Each of the plurality of electrical interconnections 1501a through 1501n extends through the intermediate layer 1301 and the second layer 1302. For example, electrical interconnection 1501a is electrically interconnected to the first electrode layer 1321 of discrete section 1309a and extends through the intermediate layer 1301 and the second layer 1302. Exposed portion 1503 of electrical interconnection 1501a is electrically interconnected to the first electrode layer 1321 of discrete section 1309a. The exposed portion 1503 may be electrically interconnected to the ultrasound imaging apparatus using methods known to those skilled in the art. Alternatively, electrical interconnections 1501a through 1501n may not extend past the bottom surface 1504 of the second layer 1302. In such a configuration, the electrical interconnections 1501a through 1501n may be interconnected to the ultrasound imaging apparatus using methods known to those skilled in the art such as, for example, wirebonding.

The electrical interconnections 1501a through 1501n may be formed by first creating holes through the intermediate layer 1301 and the second layer 1302. This may be accomplished, for example, by laser drilling. The holes may then be filled with an electrically conductive material (e.g., by a plating process). The electrical interconnections 1501a through 1501n may be configured such that a single electrical connection may be electrically interconnected to a plurality of discrete section. For example, electrical interconnection 1501a may be electrically interconnected to discrete sections 1309a and 1309b. In such a configuration, discrete sections 1309a and 1309b together may form a single transducer element and electrical interconnection 1501b may not be present. The electrical interconnections 1501a through 1501n may be oriented transverse to discrete sections to which they are electrically interconnected.

Figure 16:
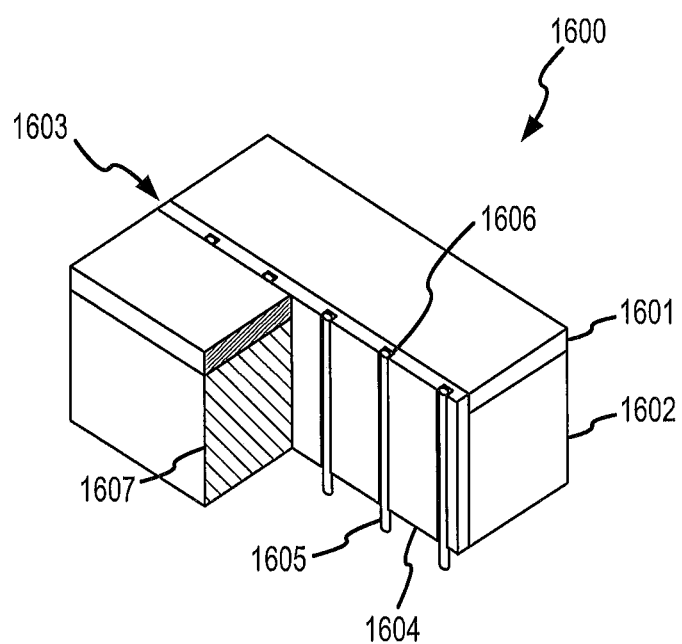
FIG. 16 is schematic view of an embodiment of a backing assembly of an ultrasonic transducer assembly.

FIG. 16 illustrates another method of electrically interconnecting the ultrasound imaging apparatus to the first electrode layer 1321 of the discrete sections of the transducer 1315. FIG. 16 is a schematic diagram of a backing assembly 1600 for use in an ultrasonic transducer assembly. To avoid repetition, the transducer array is not illustrated in FIG. 16. Rather, only the backing assembly 1600 is shown. The backing assembly 1600 is illustrated in a similar orientation to the ultrasonic transducer system 1300 of FIG. 13.

The backing assembly 1600 of FIG. 16 includes an intermediate layer 1601 and a second layer 1602. Similar to as discussed above with respect to the ultrasonic transducer system 1300, the intermediate layer 1601 may be composed of a material or materials known to those skilled in the art of ultrasonic transducer design and the second layer 1602 may be a highly attenuating material such as the materials previously described that include a woven layer of fibers made of porous polymers. The backing assembly 1600 includes an interconnection assembly 1603. The interconnection assembly 1603 may be comprised of an insulating material 1604 and individual electrical conduction members. The interconnection assembly 1603 may be disposed between sections of the intermediate layer 1601 and the second layer 1602 as illustrated in FIG. 16. A section along lines 1607 has been cut away in FIG. 16 to reveal internal details of the interconnection assembly 1603.

The individual electrical conduction members may be individual wires, such as wire 1605. The individual wires may be disposed in slots, such as slot 1606, within the insulating material and oriented transverse to the individual transducer elements. In this regard, the interconnection assembly 1603 may be comprised of a plurality of electrical interconnections passing through the backing assembly 1600. The insulating material 1604 may be composed of the same material as the intermediate layer 1601.

As noted above in reference to FIG. 1, acoustic attenuation material 114 may be placed along other surfaces within the ultrasound probe 100. Similarly in embodiments such as that illustrated in FIG. 12, the above-described acoustic attenuation materials may be used to line the housing 1201 and/or other components within the probe assembly 1200. Such application of the above-described acoustic attenuation materials may help to improve image quality by reducing the amount of unwanted acoustic energy incident upon an ultrasonic transducer array, such as transducer array 1300 of FIG. 13. Generally, the above-described acoustic attenuation materials may be positioned against a surface where a front side of the acoustic attenuation material is in a face-to-face relationship with the surface and a back side of the acoustic attenuation material is in contact with a fluid (e.g., air or water). In such a position, the acoustic attenuation material may be operable to absorb acoustic energy emanating from the surface and acoustic energy traveling through the fluid and incident upon the back side of the acoustic attenuation material.

Figure 17:
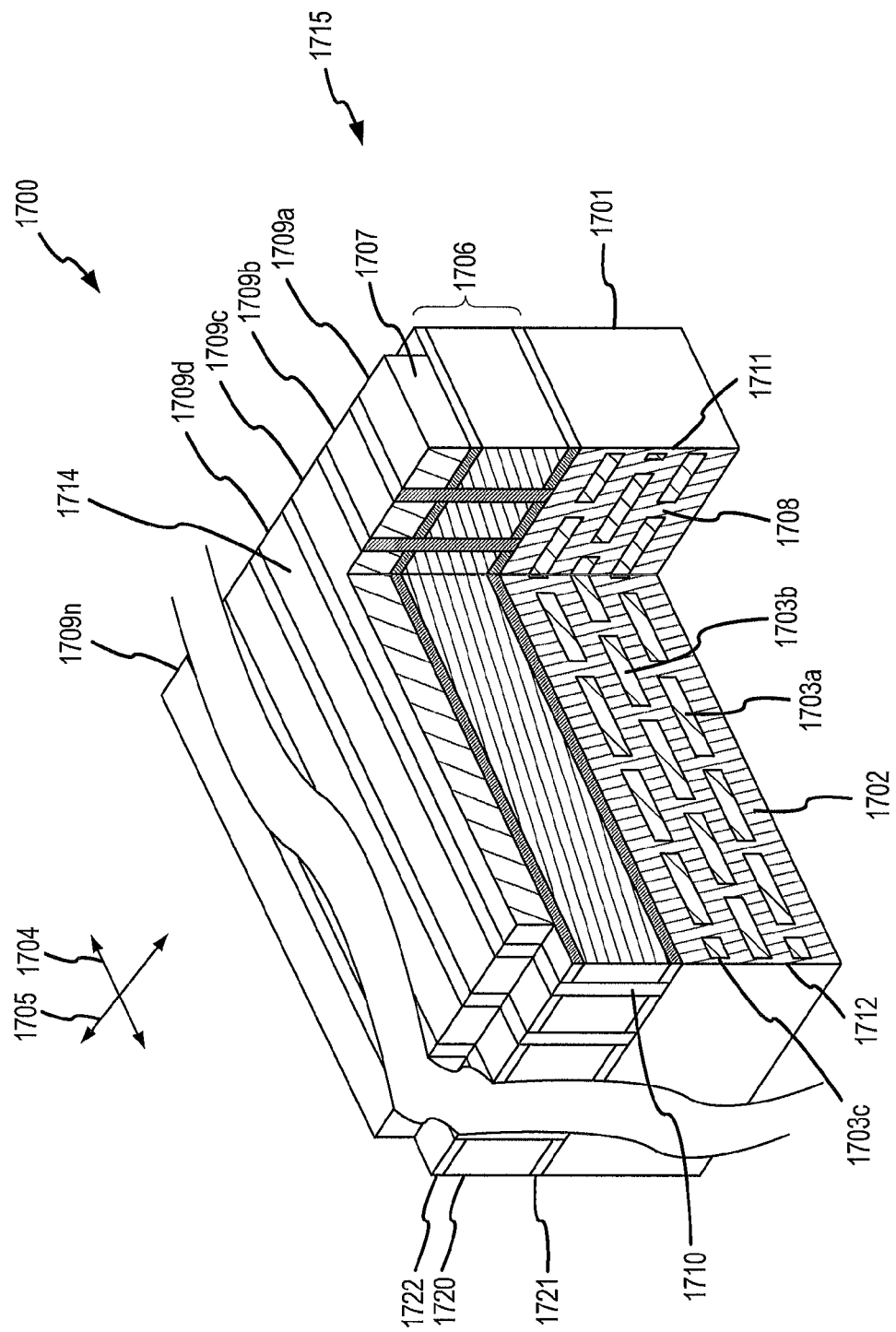
FIG. 17 is a schematic view of an embodiment of an ultrasonic transducer.

Turning to FIG. 17, a cross-sectional schematic view of an ultrasonic transducer system 1700 is presented. A section along lines 1711 and 1712 has been cutaway in FIG. 17 to reveal internal details of the ultrasonic transducer system 1700. The ultrasonic transducer system 1700 has a longitudinal axis 1705 and an elevation axis 1704. The ultrasonic transducer system 1700 is comprised of a predetermined number of discrete sections represented in FIG. 17 by discrete sections 1709a through 1709n, where n represents the predetermined number of discrete sections. The ultrasonic transducer system 1700 is shown as a one-dimensional array with a single row of n transducers, where n represents a predetermined number of discrete sections. Alternatively, the ultrasonic transducer system 1700 may comprise a two-dimensional array of discrete section arranged in multiple rows and multiple columns.

Generally, as is known to those skilled in the art, a transducer 1715 (comprising of a piezoelectric layer 1706 and any optional matching layer attached thereto) may be divided into a predetermined number of discrete sections represented in FIG. 17 by discrete sections 1709a through 1709n arranged along the longitudinal axis 1705. Similarly to as discussed with reference to FIG. 13, these discrete sections may each form a transducer element or they may be electrically combined so that two or more discrete sections may form a transducer element. A backing 1701, described below, may also be present.

The transducer 1715 may include a piezoelectric layer 1706. The piezoelectric layer 1706 may include a layer of piezoelectric material 1720, a first electrode layer 1721 and a second electrode layer 1722. The layer of piezoelectric material 1720 may be comprised of a ceramic-based material. The first electrode layer 1721 may be comprised of one or more layers of electrically conductive material. Similarly, the second electrode layer 1722 may be comprised of one or more layers of electrically conductive material. The portion of the first electrode layer 1721 connected to each individual transducer element may serve as the signal electrode for that individual transducer element. Similarly, the second electrode layer 1722 may serve as the ground electrode. The individual transducer element electrodes may be interconnected to electronic circuitry, which may provide for acoustic wave generation and sensing. Optional acoustic matching layers may be interconnected to the piezoelectric layer 1706.

The ultrasonic transducer system 1700 of FIG. 17 shows a single optional matching layer 1707. The presence and number of optional matching layers may vary from the configuration illustrated in FIG. 17. The transducer 1715 comprises the piezoelectric layer 1706, along with any optional matching layers attached thereto.

The piezoelectric layer 1706 may be a mechanically active layer operable to convert electrical energy to mechanical energy and mechanical energy into electrical energy and may be comprised of any of the materials discussed above with reference to the piezoelectric layer 1306 of FIG. 13. The transducer 1715 of FIG. 17 includes an acoustic face 1714. Each individual transducer element may be separated from neighboring elements by kerfs (e.g., kerf 1710 between discrete sections 1709c and 1709d) produced during the dicing of the transducer 1715.

The backing 1701 of the ultrasonic transducer system 1700 may comprise the composite material described above with reference to FIG. 11. In this regard, the backing 1701 may include one or more porous-polymer sheets, such as sheets 1703a, 1703b and 1703c interleaved with layers of a support material 1702. The support material may, for example, be comprised of an epoxy. Each of the porous-polymer sheets 1703a, 1703b and 1703c may be composed of porous PTFE. Each of the porous-polymer sheets 1703a, 1703b and 1703c may include a plurality of through holes, such as through hole 1708. The plurality of through holes may be at least partially filled with the support material 1702.

FIG. 17 illustrates a backing 1701 containing three layers of porous-polymer sheets 1703a, 1703b and 1703c. Various embodiments may use a single porous-polymer sheet, two porous-polymer sheets, or four or more porous-polymer sheets. Hole patterns in the porous-polymer sheets may vary from that illustrated in FIG. 17. The hole size, quantity and pattern may be varied to achieve desired mechanical and/or acoustic properties.

As shown in FIG. 17, the support material 1702 completely encapsulates the porous-polymer sheets 1703a, 1703b and 1703c. Such a configuration may be achieved by precutting the individual porous-polymer sheets 1703a, 1703b and 1703c and then encapsulating them within the support material 1702.

Alternatively, the backing 1701 may be produced in sizes larger than what would be required for a single ultrasonic transducer system 1700. For example, a sheet of backing material several times larger than that required for a single ultrasonic transducer system 1700 may be provided. A similarly sized layer of piezoelectric material may be interconnected to the sheet of backing material along with any optional matching layers that may be desired. This assembly may then be diced to produce kerfs between strips of piezoelectric material. The kerfs may then be filled. The entire assembly could then be cut into individual ultrasonic transducer systems such as the ultrasonic transducer system 1700 of FIG. 17.

In this regard, the backing 1701 may be reduced to its final size (e.g., by slicing) with the edges of the individual porous-polymer sheets 1703a, 1703b and 1703c exposed along the sides of the backing 1701. Depending on the application and working environment of the ultrasonic transducer system 1700, the edges of the individual porous-polymer sheets 1703a, 1703b and 1703c may remain exposed or the edges may be sealed in a manufacturing step (e.g., by placing a layer of epoxy around the edges of the backing 1701). The edges may be sealed to, for example, prevent substances from entering the pores of the porous-polymer sheets or to provide additional mechanical integrity.

Electrical interconnection to the individual transducer elements of the ultrasonic transducer system 1700 may be achieved in manner similar to as discussed above with respect to the ultrasonic transducer system 1300 of FIG. 13. For example, the electrical interconnections to the first electrode layer 1721 of each individual transducer element may be achieved by electrically interconnecting to the first electrode layer 1721 along an the edge of the transducer 1715. For example, the electrical interconnections to the first electrode layer 1721 may be achieved by electrically connecting through the backing 1701 in a manner similar to that described above with reference to FIG. 15 (e.g., drilling through the backing 1701 and plating) and FIG. 16 (e.g., using an interconnection assembly similar to the interconnection assembly 1603).

Once situated in, for example, an ultrasound probe, the ultrasonic transducer system 1700 may be oriented such that the acoustic face 1714 is in proximity to an outer portion of the ultrasound probe. Accordingly, the rear of the ultrasonic transducer system 1700 (e.g., the rear face of the backing 1701 opposite from the piezoelectric layer 1706) may face away from the outer portion of the ultrasound probe and toward an internal portion of the ultrasound probe. In this regard, the rear face of the backing 1701 may be exposed to an internal environment of the ultrasound probe that may, for example, contain air.

FIG. 17 shows the ultrasonic transducer system 1700 as being straight along the elevation axis 1704. In an alternate configuration, the individual transducer elements of the ultrasonic transducer system 1700 may be curved along the elevation axis 1704.

FIG. 17 illustrates the ultrasonic transducer system 1700 with a backing 1701 similar to the material described with reference to FIGS. 9-11. It is noted that the ultrasonic transducer system 1700 may also be configured using the backing materials described with reference to FIGS. 8A and 8B.

Figure 18:
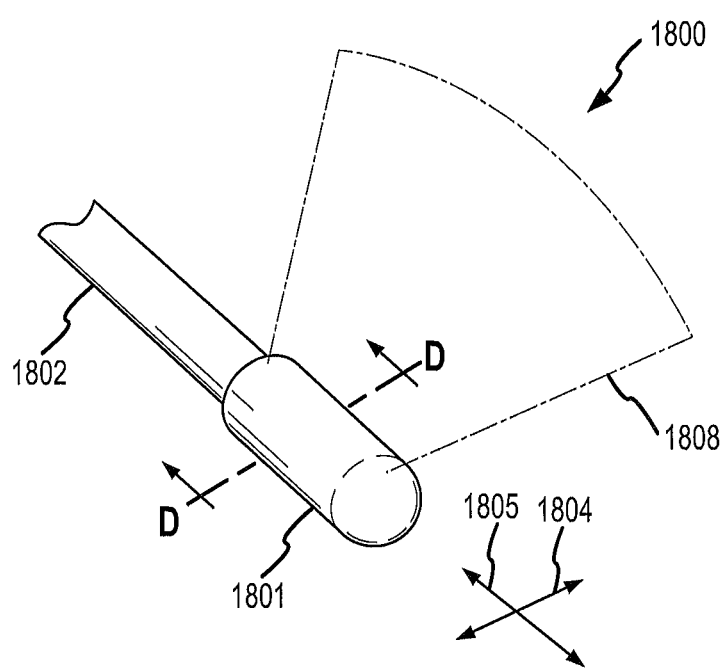
FIG. 18 is an isometric view of an embodiment of an ultrasound probe assembly contained within a catheter.
Figure 19:
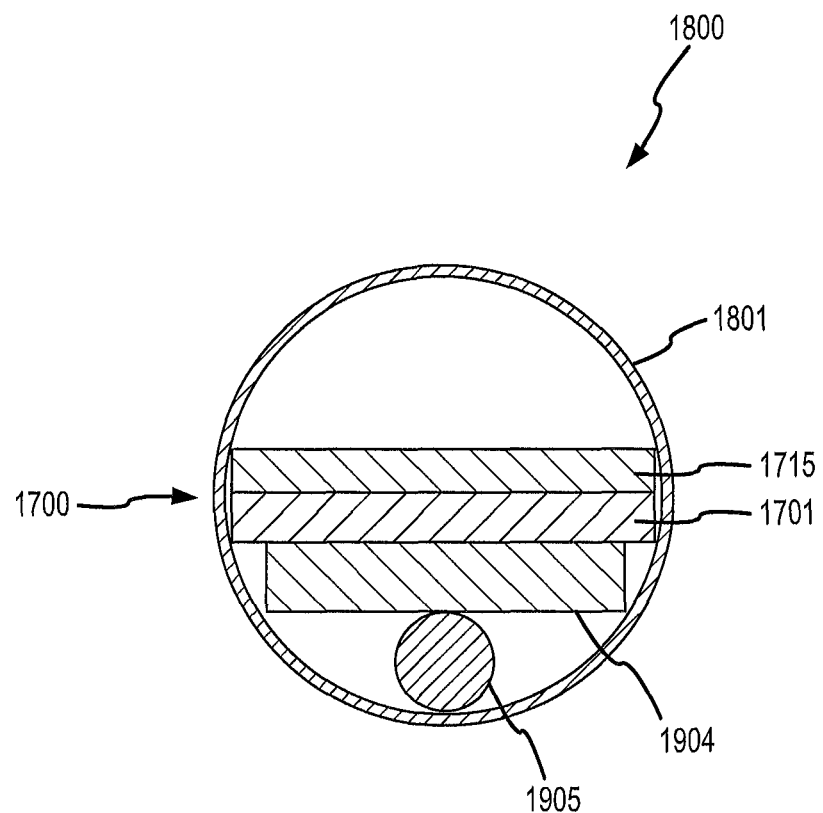
FIG. 19 is a cross sectional view of the catheter of FIG. 18.

FIGS. 18 and 19 illustrate an exemplary application of the ultrasonic transducer system 1700 of FIG. 17. FIG. 18 illustrates a catheter 1800 that contains an ultrasonic transducer. The catheter 1800 comprises an outer shell 1801 surrounding an ultrasonic transducer and an interconnected tube 1802. The tube 1802 may contain electrically conductive pathways to electrically interconnect the ultrasonic transducer with an ultrasound imaging apparatus (not shown). The ultrasonic transducer within the catheter 1800 may be oriented along a longitudinal axis 1805 and an elevation axis 1804 so that a beam of acoustic energy may be swept through an imaging plane 1808.

The ultrasonic energy, in the form of acoustic waves, may be directed into the internal structure of a patient. The acoustic waves may interact with and reflect off of various internal features. These reflections may then be detected by ultrasonic transducer within the catheter 1800 and displayed as images of the internal structure of the patient by the ultrasound imaging apparatus.

FIG. 19 is a cross sectional view along section line D-D of the catheter 1800 of FIG. 18. The ultrasonic transducer system 1700, comprising the transducer 1715 and the backing 1701, is disposed within the outer shell 1801. The catheter 1800 also includes an electrical interconnection assembly 1904 that electrically interconnects to the ultrasonic transducer system 1700. The electrical interconnection assembly 1904 may, for example, be a GORE™ MicroFlat Ribbon Cable available from W. L. Gore & Associates, Inc., Newark, Del., U.S.A. The catheter 1800 may also include a working channel 1905.

The backing 1701 may, for example, be constructed in accordance with the embodiments described with reference to FIGS. 8A through 11. It will be appreciated that since the backing 1701 may be comprised of porous-polymer sheets that have a high attenuation per unit thickness (relative to traditional ultrasonic transducer backing materials), the backing 1701 may be thinner than a backing of similar attenuation capability made from traditional backing materials (e.g., epoxy, silicone rubber). The thinner, rigid backing 1701 has several advantages. For example, in a round catheter such as catheter 1800, as the backing thickness is decreased, the maximum width of the ultrasonic transducer system 1700 may be increased. Also, as the backing thickness is decreased, the room available for other components within the catheter is increased and/or the overall size of the catheter may be decreased. The rigidity of the backing 1701 also is operable to support and/or position the transducer 1715 without the need for supplemental support members. Additionally, the above-described methods of electrically interconnecting to the transducer 1715 through the backing 1701 may result in no need for electrical connections along the edges of the transducer 1715 and therefore the transducer 1715 and backing 1701 may extend to, or close to, the outer shell 1801 of the catheter 1800.

Figure 20:
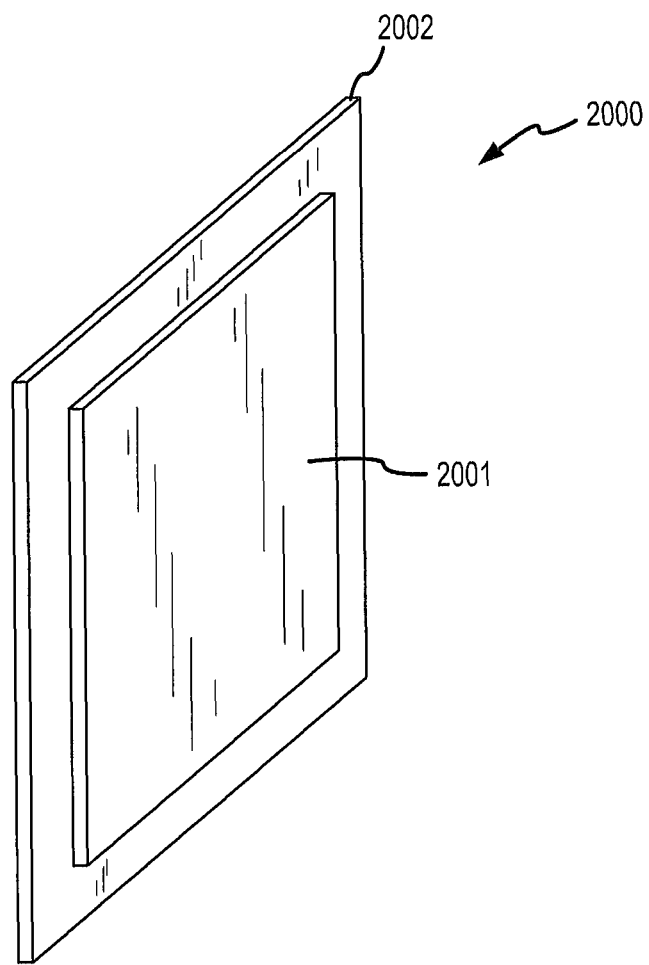
FIG. 20 is an isometric view of an acoustic attenuation material interconnected to a support structure.

The acoustic attenuation materials described herein may be used in a wide variety of locations. As noted above, the acoustic attenuation materials may be used to line the interior of the housing 1201 of probe assembly 1200. FIG. 20 illustrates an exemplary embodiment where acoustic attenuation material 2001 is interconnected (e.g., bonded with epoxy) to a support structure 2002 to form an acoustic energy-absorbing panel 2000. Such a panel 2000 may be positioned in a wide variety of locations to absorb acoustic energy. For example, the panel may be situated within a predetermined volume where it is desired to reduce the level of acoustic energy within that predetermined volume. The panel 2000 may include one or more of the above-described acoustic attenuation materials.

Figure 21:
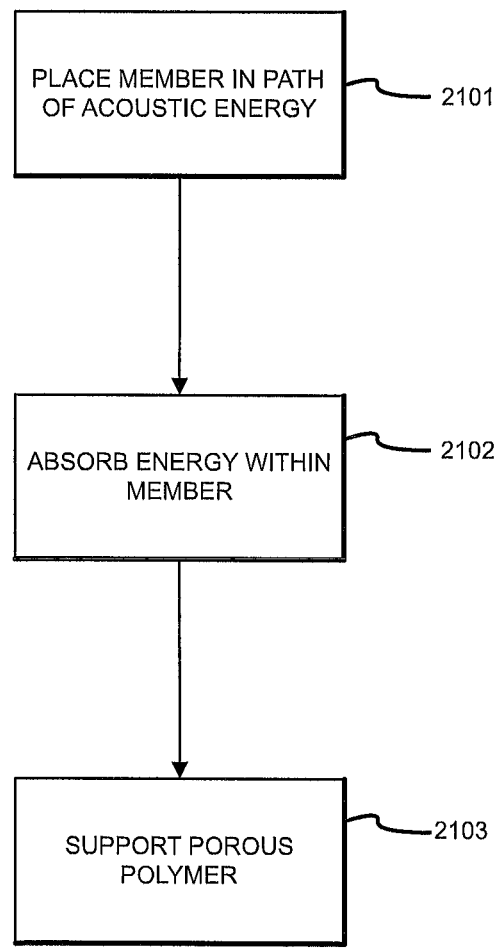
FIG. 21 is a flow diagram of a method of attenuating acoustic energy.

FIG. 21 is a flow diagram of a method of attenuating acoustic energy. Although the flow diagram illustrates particular steps in a particular order, this is for exemplary purposes only and the order of the steps may be rearranged from that depicted in FIG. 21. The first step 2101 includes placing a member in the path of acoustic energy to be attenuated. The member may comprise a porous polymer and support material. The porous polymer may include PTFE, urethane, polystyrene, silicone, fluoropolymer, polyolefin (e.g., polyethylene and polypropylene) or a combination thereof.

The porous polymer may be in the form of one or more layers of woven fibers. The support material may occupy a portion of the void space between the woven fibers.

The porous polymer may be in the form of a plurality of individual layers of non-woven sheets. For example, a plurality of layers of porous polymer may be interleaved with a plurality of layers of support material. The sheets may be continuous or the sheets may be perforated. In embodiments where the sheets are perforated, the support material may at least partially fill the perforations.

The placing may include placing the member adjacent to a surface where a front side of the member is in contact with the surface. The placing may include placing the member within a predetermined volume to damp acoustic energy within the predetermined volume.

The second step 2102 may be to absorb at least a portion of the acoustic energy within the member. In embodiments where the member is placed adjacent to a surface, the absorbing may include absorbing acoustic energy emanating from the surface and absorbing acoustic energy incident of a rear side of the member within the member.

The third step 2103 may be to support the porous polymer with the support material. This may, for example, be achieved my encapsulating a layer of woven porous polymer within a matrix of support material, or by interleaving a plurality of layers of porous polymer with a plurality of layers of support material.

Figure 22:
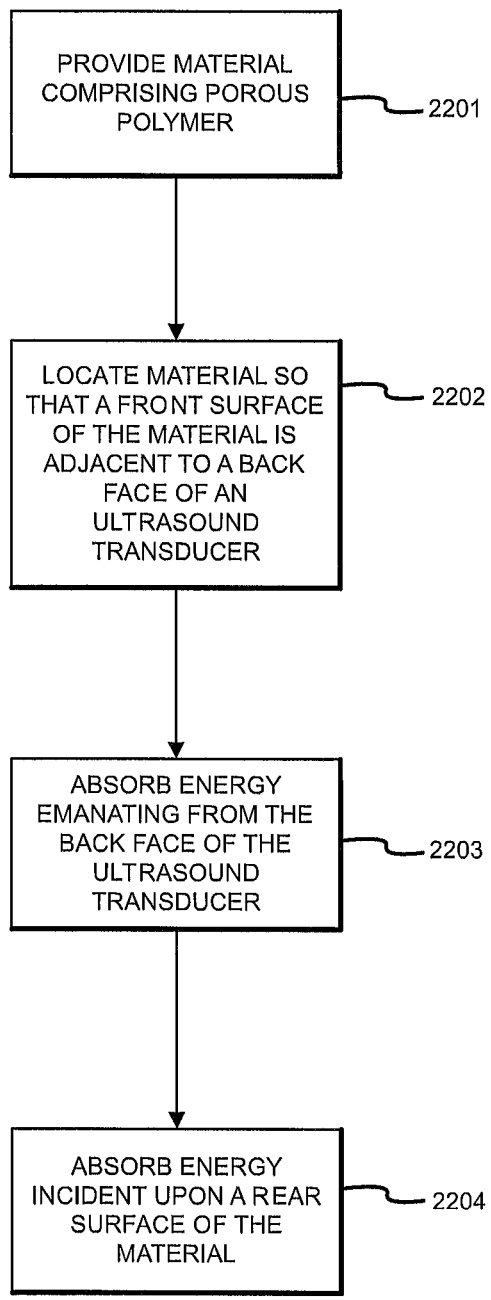
FIG. 22 is a flow diagram of a method of reducing acoustic energy incident on a back face of an ultrasound transducer.

FIG. 22 is a flow diagram of a method of reducing acoustic energy incident on a back face of an ultrasound transducer. Although the flow diagram illustrates particular steps in a particular order, this is for exemplary purposes only and the order of the steps may be rearranged from that depicted in FIG. 22. The acoustic energy may have a frequency between 100 kHz and 100 MHz.

The first step 2201 includes providing a layer of material comprising a porous polymer. The porous polymer may be woven or non-woven. The layer of material may have a front surface and a rear surface. The layer of material may also include support material. In embodiments including woven porous polymers, a layer of woven porous polymer may be encapsulated within a matrix of support material.

In embodiments including non-woven porous polymer, the non woven porous polymer may be in the form of a plurality of sheets interleaved with a plurality of sheets of support material. The sheets may be continuous or the sheets may be perforated. In embodiments where the sheets are perforated, the support material may at least partially fill the perforations.

The second step 2202 may be to locate the material so that the front surface of the material is adjacent to a back face of an ultrasound transducer in a face-to-face relationship. The back surface of the material may be in contact with a fluid such as a gas. The fluid may, for example, be air contained within an ultrasound probe casing or within a catheter that contains an ultrasound transducer.

The next step 2203 may be to absorb acoustic energy emanating from the back face of the ultrasound transducer. The following step 2204 may be to absorb acoustic energy incident upon the rear surface of the material. In this regard, the absorbed energy may be prevented from reaching the back face of the ultrasound transducer and interfering with the operation of the ultrasound transducer.

Although the above detailed description generally describes embodiments related to acoustic attenuation materials and ultrasound probe assemblies, embodiments described herein may be utilized in other applications where acoustic attenuation is desired and in other ultrasonic transducer configurations.

Additional modifications and extensions to the embodiments described above will be apparent to those skilled in the art. Such modifications and extensions are intended to be within the scope of the present invention as defined by the claims that follow.

The invention claimed is:

1. Acoustic attenuation material comprising:
a first side;
a second side oppositely disposed from said first side;
a polymer having a porosity, said polymer comprising at least one of a woven layer having a porosity and a non-woven membrane having a porosity; and
a reinforcing material, wherein acoustic attenuation of said polymer is at least twice that of said reinforcing material, wherein said reinforcing material has a flexural modulus greater than that of the polymer having a porosity, and wherein said polymer and said reinforcing material are configured such that a sound beam traveling from said first side to said second side must pass through at least a portion of said polymer.

2. The acoustic attenuation material of claim 1, wherein said polymer having said porosity has a first flexural modulus; and
wherein said acoustic attenuation material has an overall flexural modulus of at least twice that of said first flexural modulus.

3. The acoustic attenuation material of claim 2, wherein said reinforcing material has a second flexural modulus, and wherein said first flexural modulus is less than 20 Mpa and said second flexural modulus is at least 40 Mpa.

4. The acoustic attenuation material of claim 1, wherein said polymer is selected from a group consisting of PTFE, urethane, polystyrene, fluoropolymer, silicone and polyolefin, wherein said reinforcing material is selected from a group consisting of polymer, ceramic and metal.

5. The acoustic attenuation material of claim 1, wherein said reinforcing material is selected from a group consisting of epoxy, THV, FEP, PTFE, PES, EFEP, PET, PEEK, PEI, PC and LCP.

6. The acoustic attenuation material of claim 1, wherein said porosity is at least 5 percent.

7. The acoustic attenuation material of claim 1, wherein said acoustic attenuation material has an acoustic attenuation of at least 25 dB/cm at 1 MHz with respect to sound traveling from said first side to said second side.

8. The acoustic attenuation material of claim 1, wherein said porosity is partially filled with said reinforcing material.

9. The acoustic attenuation material of claim 8, wherein said polymer comprises a woven layer having voids at least partially filled with said reinforcing material.

10. The acoustic attenuation material of claim 9, wherein said reinforcing material encapsulates said woven layer.

11. The acoustic attenuation material of claim 1, wherein said polymer comprises a plurality of non-woven membranes, wherein said reinforcing material comprises a plurality of support layers, and wherein said plurality of non-woven membranes are interleaved with said plurality of support layers.

12. The acoustic attenuation material of claim 11, wherein each of said plurality of non-woven membranes comprises a plurality of vias defining a plurality of passageways through said plurality of non-woven membranes, wherein at least a portion of said plurality of vias are filled with said reinforcing material.

13. The acoustic attenuation material of claim 12, wherein said porous polymer is selected from a group consisting of PTFE, urethane, polystyrene, fluoropolymer, silicone, and polyolefin.

14. The acoustic attenuation material of claim 13, wherein said reinforcing material is selected from a group consisting of epoxy, THV, FEP, PTFE, PES, EFEP, PET, PEEK, PEI, PC, and LCP.

15. The acoustic attenuation material of claim 11, wherein each of said plurality of membranes has a thickness less than 800 microns, wherein each of said plurality of support layers has a thickness less than 500 microns.

16. The acoustic attenuation material of claim 1, wherein said polymer comprises at least one non-woven membrane, and wherein said reinforcing material comprises at least one support layer comprising a different polymer.

17. The acoustic attenuation material of claim 1, wherein said polymer comprises at least one membrane comprising PTFE and having a first flexural modulus, and wherein said reinforcing material comprises at least one support layer having second flexural modulus at least twice the first flexural modulus.

18. Acoustic attenuation material comprising:
a first side;
a second side oppositely disposed from said first side;
a polymer having a porosity, said polymer comprises a plurality of non-woven membranes; and
a reinforcing material, wherein acoustic attenuation of said polymer is at least twice that of said reinforcing material, wherein said reinforcing material has a flexural modulus greater than that of the polymer having a porosity, wherein said reinforcing material comprises a plurality of support layers, wherein said plurality of non-woven membranes are interleaved with said plurality of support layers, and wherein said plurality of non-woven membranes and said plurality of support layers are configured such that a sound beam traveling from said first side to said second side must pass through at least a portion of said plurality of non-woven membranes.

19. The acoustic attenuation material of claim 18, wherein each of said plurality of non-woven membranes comprises a plurality of vias defining a plurality of passageways through said plurality of non-woven membranes, wherein at least a portion of said plurality of vias are filled with said reinforcing material.

20. The acoustic attenuation material of claim 18, wherein said porosity is partially filled with said reinforcing material.

21. The acoustic attenuation material of claim 18, wherein each of said plurality of membranes has a thickness less than 800 microns, wherein each of said plurality of support layers has a thickness less than 500 microns.

* * * * *